United States Patent [19]

Fujita et al.

[11] 4,246,414

[45] Jan. 20, 1981

[54] 2-ALKOXYALKOXY-5-NITROBENZENE-SULFONIC ACID AND SALT THEREOF

[75] Inventors: Shinsaku Fujita; Shigetoshi Ono; Hidetoshi Hayashi, all of Minami-ashigara, Japan

[73] Assignee: Fuji Photo Film Co., Ltd., Minami-ashigara, Japan

[21] Appl. No.: 69,647

[22] Filed: Aug. 27, 1979

Related U.S. Application Data

[63] Continuation of Ser. No. 917,759, Jun. 21, 1978, abandoned.

[30] Foreign Application Priority Data

Jun. 21, 1977 [JP] Japan .................................. 52-74601

[51] Int. Cl.³ .................. C07D 215/10; C07D 213/04; C07C 143/55
[52] U.S. Cl. ...................................... 546/182; 546/347; 260/512 R; 260/199; 260/198; 430/223
[58] Field of Search .......................... 260/512 R, 509; 546/182, 347

[56] References Cited

U.S. PATENT DOCUMENTS 4,041,024  8/1977  Wolfrüm et al. .................... 260/509

FOREIGN PATENT DOCUMENTS 1416574  12/1975  United Kingdom ................ 260/512 R

OTHER PUBLICATIONS

Bartoszewicz et al., Chem. Abstract, 52, 4536b, (1957).

*Primary Examiner*—Nicky Chan
*Attorney, Agent, or Firm*—Sughrue, Rothwell, Mion, Zinn and Macpeak

[57] ABSTRACT

A 2-alkoxyalkoxy-5-nitrobenzenesulfonic acid or a salt thereof represented by the following general formula (I):

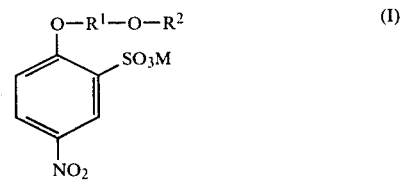

wherein $R^1$ represents an alkylene group having 2 or more carbon atoms; $R^2$ represents an alkyl group; and M represents an inorganic or organic cation. The compound represented by the general formula (I) is useful as an intermediate for a dye releasing redox compound which is suitable for use in the color diffusion transfer process.

8 Claims, 4 Drawing Figures

2-ALKOXYALKOXY-5-NITROBENZENESULFONIC ACID AND SALT THEREOF

This is a continuation of application Ser. No. 917,759, filed June 21, 1978 now abandoned.

BACKGROUND OF THE INVENTION

1. Field of the Invention

The present invention relates to a compound useful as an intermediate for a dye releasing redox compound which is suitable for use in the color diffusion transfer process and, more particularly, to a compound useful as an intermediate for a dye releasing redox compound having an improved transferability and light fastness.

2. Description of the Prior Art

Color diffusion transfer color image forming processes using a dye releasing redox compound are described in U.S. Pat. Nos. 3,928,312, 3,931,144, 3,929,760, 3,932,381, 3,954,476, U.S. Patent Application Document B-351,673, West German Patent Application (OLS) 2,505,248, and Research Disclosure, No. 13024 (1957). The term "dye releasing redox compound" means a compound containing therein a group referred to as a redox moiety and a dye (including a dye precursor) moiety. The redox moiety renders the redox compound immobile due to a ballast group attached thereto, but the compound per se splits and releases a compound having the dye moiety (dye compound) due to a redox reaction under alkaline conditions. For instance, a light-sensitive element having a light-sensitive silver halide emulsion layer and a redox compound associated therewith is exposed and developed with an alkaline processing solution, whereby the redox compound per se is oxidized in proportion to the amount of developed silver halide and then splits into a compound having a dye moiety (dye compound) and a nondiffusible quinone compound due to the alkaline processing solution. As a result, the compound having a dye moiety diffuses into an image receiving layer to provide a transferred image therein.

Examples of redox compounds which release cyan dye compounds are described in U.S. Pat. Nos. 3,929,760 and 3,942,987, etc. Examples of redox compounds which release magenta dye compounds are described in U.S. Pat. Nos. 3,954,476, 3,931,144 and 3,932,380, etc. Examples of redox compounds which release yellow dye compounds are described in U.S. Pat. No. 4,013,633, etc. However, using these prior art dye releasing redox compounds, technical problems are encountered in that the transferred images have insufficient stability (for example, the light fastness of the images is not sufficient and the images fade to a large extent under light) and in that the transfer of the dye compounds is not sufficient.

The insufficient transferability and light fastness of the dye compound result from the structure of the redox moiety in the redox compound. That is, a typical known redox moiety is an o- or p-hydroxyarylsulfamoyl group having a ballast group. On the contrary, it was found that when a redox compound in which an aminosulfonyl (sulfamoyl) or aminocarbonyl (carbamoyl) group substituted with a phenyl group to which an alkoxy group and a known redox moiety are bonded at the para position and the meta position, respectively, is used as a redox moiety, a markedly improved transferability and light fastness is achieved in the dye compound.

SUMMARY OF THE INVENTION

A first object of the present invention is to provide a compound useful as an intermediate for a dye releasing redox compound having a novel redox moiety which improves the transferability of the dye compound (cyan, magenta or yellow dye) formed therefrom.

A second object of the present invention is to provide a compound useful as an intermediate for a dye releasing redox compound providing a dye image whose hue is excellent.

A third object of the present invention is to provide a compound useful as an intermediate for a dye releasing redox compound from which a stable dye image is obtained.

The above-described objects are accomplished with a 2-alkoxyalkoxy-5-nitrobenzenesulfonic acid or a salt thereof represented by the following general formula (I):

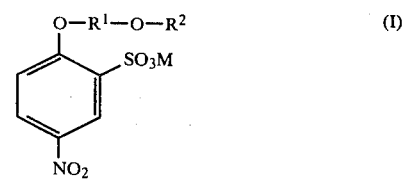

wherein $R^1$ represents an alkylene group having 2 or more carbon atoms; $R^2$ represents an alkyl group; and M represents a cation.

BRIEF DESCRIPTION OF THE ACCOMPANYING DRAWINGS

FIGS. 1 to 4 of the drawings show the infrared absorption spectra for Compounds (I-A) to (I-C) and (I-E) of the present invention, respectively.

DETAILED DESCRIPTION OF THE INVENTION

Figure 1:
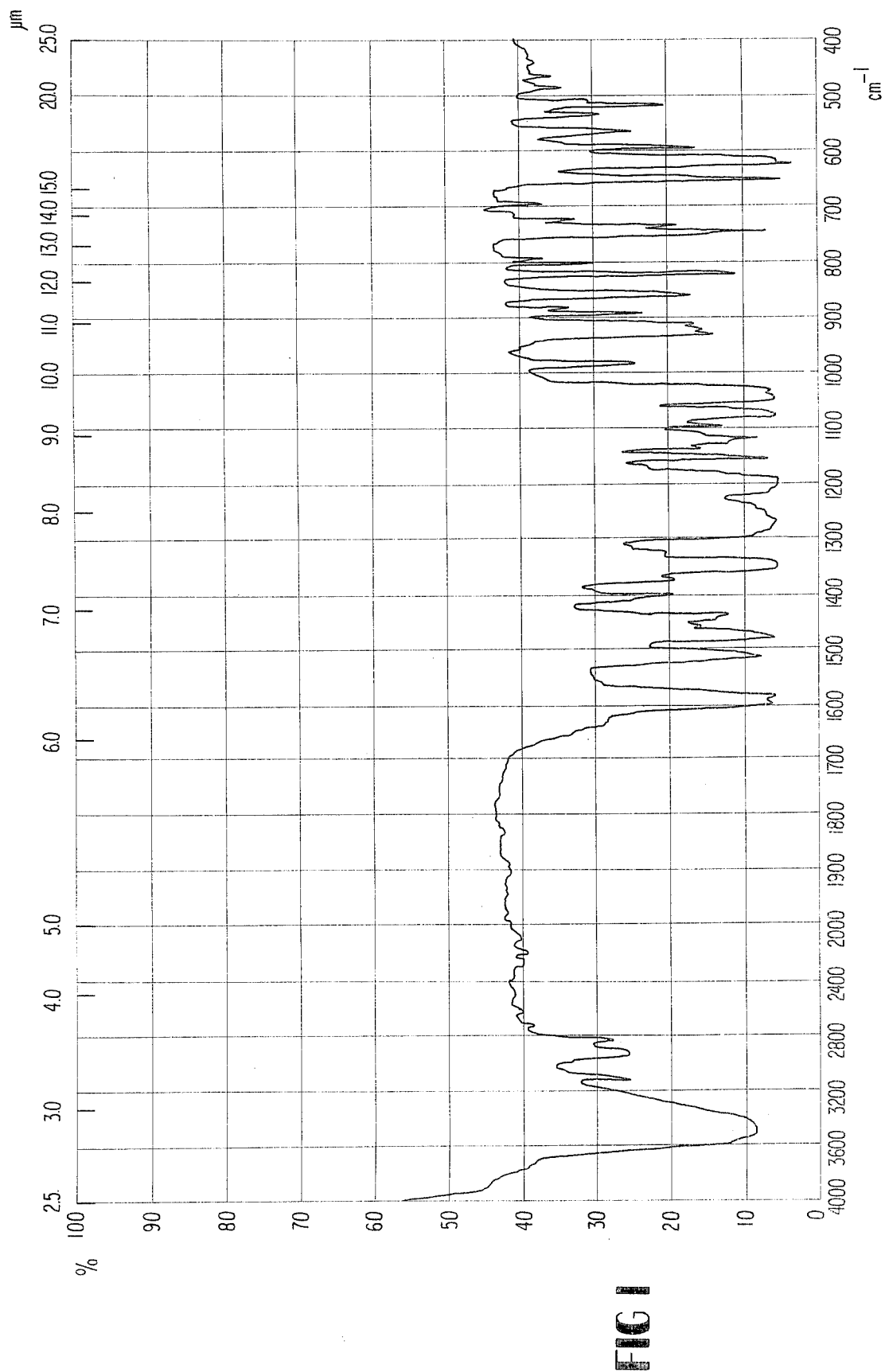

The alkylene group having 2 to 15 carbon atoms represented by $R^1$ can be a straight chain or branched chain alkylene group and an alkylene group having 2 to 8 carbon atoms is preferred. Although $R^1$ can be a branched chain alkylene group, a branched chain alkylene group which forms an acetal linkage is excluded. Particularly preferred examples of $R^1$ are a straight chain alkylene group represented by the formula $—(CH_2)_p—$, wherein p is an integer of 2 to 4, and a branched chain alkylene group having 3 to 4 carbon atoms such as $—CH(CH_3)CH_2—$ and $—CH_2CH_2CH(CH_3)—$ with an alkylene group which forms an acetal linkage being excluded as described above. In view of easy availability of starting materials to produce the dye-releasing redox compounds of this invention, a $—CH_2CH_2—$ group is particularly advantageous for $R^1$. When $R^1$ represents a methylene group, an acetal linkage, such as $—O—CH_2—O—R^2$, is formed, which is undesirable since it is chemically unstable (particularly under acidic conditions) and tends to decompose during the preparation thereof. For the same reason, groups where two oxygen atoms are bonded to the same carbon atom in the $—O—R^1—O—R^2$ group (i.e., forming an acetal linkage), are also not desirable.

The alkyl group represented by $R^2$ can be a straight chain or branched chain alkyl group and preferably is an alkyl group having 1 to 8 carbon atoms. A particularly preferred example of an alkyl group for $R^2$ is a straight chain or branched chain alkyl group having 1 to 4 carbon atoms (for example, a methyl group, an ethyl group, an n-propyl group, an isopropyl group, an n-butyl group, etc.). From the standpoint of the preparation of the compounds represented by the general formula (I) above, a straight chain alkyl group having 1 to 4 carbon atoms is particularly advantageous for $R^2$.

M can be an inorganic cation or an organic cation, either monovalent or divalent which is bonded stoichiometrically.

Examples of inorganic cations represented by M include a hydrogen ion, an alkali metal ion and an alkaline earth metal ion. Suitable alkali metal ions for M include a lithium ion, a sodium ion and a potassium ion. Suitable alkaline earth metal ions for M include a magnesium ion, a calcium ion and a barium ion.

For the organic cation represented by M, a quaternary nitrogen atom-containing heteroaromatic ring (for example, a pyridinium ion and a nucleus substituted derivative thereof, a quinolinium ion and a nucleus substituted derivative thereof, etc.) is preferred.

Of the above-described ions, an alkali metal ion is particularly preferred for M. A sodium ion is particularly advantageous for M because of ease in preparation and the starting material is inexpensive.

In summary, particularly preferred compounds according to the present invention are those in which the substituents in the above-described general formula (I) are as follows: $R^1$ represents a —CH$_2$CH$_2$— group; $R^2$ represents a straight chain or branched chain alkyl group having 1 to 4 carbon atoms; and M represents an alkali metal ion (such as a sodium ion or a potassium ion, etc.).

Even more preferred compounds are those in which the substituents in the above-described general formula (I) are as follows: $R^1$ represents a —CH$_2$CH$_2$— group; $R^2$ represents a straight chain alkyl group having 1 to 4 carbon atoms (a methyl group, an ethyl group, an n-propyl group or an n-butyl group); and M represents a sodium ion.

Specific examples of compounds and salts represented by the general formula (I) above according to the present invention (hereinafter compounds according to the present invention) are shown below. However, the present invention is not to be construed as being limited to these compounds.

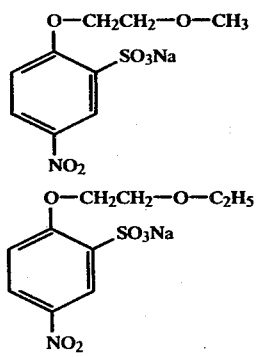

Compound (I-A)

Compound (I-B)

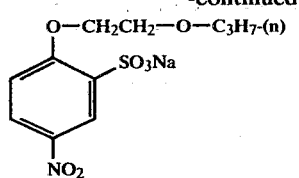

Compound (I-C)

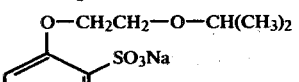

Compound (I-D)

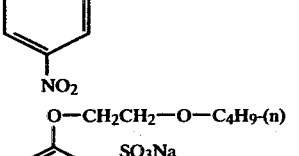

Compound (I-E)

Compounds according to the present invention also include those compounds where the sodium ion in Compounds (I-A) to (I-E) is replaced by a potassium ion, a calcium ion, a barium ion, a magnesium ion, a pyridinium ion or a hydrogen ion, i.e., the compound is the free sulfonic acid.

A known compound which might be considered on superficial examination to be similar to the compound of the present invention is 2-methoxy-5-nitrobenzenesulfonic acid as described in *Chemical Abstracts*, Vol. 52, 4536b; *Lodz. Towarz. Nauk., Acta Chim.*, Vol. 2, pages 95 to 99 (1957). On review it can be seen that the methoxy group in the 2-position is unsubstituted whereas the alkoxy group in the 2-position of the compound according to the present invention is substituted with an alkoxy group, i.e., the substituent in the 2-position of the compound according to this invention is an alkoxyalkoxy group.

A first method for preparation of the compound according to the present invention comprises reacting a compound represented by the general formula (A):

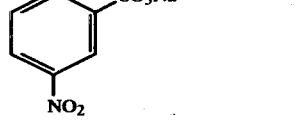

(A)

wherein Hal represents a halogen atom (preferably a chlorine atom); and M has the same meaning as defined in the general formula (I), with an alkoxide represented by the general formula (B):

$$R^2\text{—O—}R^1\text{—ONa} \qquad (B)$$

wherein $R^1$ and $R^2$ each has the same meaning as defined in the general formula (I). The alkoxide represented by the formula (B) can be obtained by treating an alcohol of the formula $R^2$—O—$R^1$—OH with metallic sodium or sodium hydride. While the alkoxide of the formula $R^2$—O—$R^1$—ONa can be isolated by distilling off the excess amount of the alcohol of the formula $R^2$—O—$R^1$—OH, usually a solution of the alkoxide of the formula $R^2$—O—$R^1$—ONa in the alcohol of the formula $R^2$—O—$R^1$—OH is preferably used in the following step. The alkoxide of the formula $R^2$—O—$R^1$—ONa is used in an amount of from about 1 mol to about 50 mol, preferably from about 1 mol to about 10 mol, and more preferably, from about 1 mol to about 3 mol, per mol of the compound having the formula (A). A suitable reaction temperature ranges from about $-20°$ C. to about $150°$ C., preferably from $0°$ C. to $100°$ C., and more preferably from $30°$ C. to $85°$ C., in order to control the formation of by-products. The compounds represented by the general formulas (A) and (B) used in this synthesis are commercially available compounds.

A second method for preparation of the compound according to the present invention comprises treating a compound having the formula (A) in an alcohol having the formula $R^2$—O—$R^1$—OH with sodium hydroxide or potassium hydroxide in the presence of manganese dioxide. Sodium hydroxide is preferably used in this method. More particularly, 1 mol of a compound of the formula (A) and from about 10 g to about 1 kg, preferably from about 10 g to about 500 g, more preferably from about 30 g to about 100 g, are suspended in from about 100 ml to about 50 l, preferably from about 300 ml to about 5 ml, more preferably from about 400 ml to about 2 l, of an alcohol having the formula $R^2$—O—$R^1$—OH and then treated with from about 1 mol to about 50 mol, preferably from about 1 mol to about 10 mol, more preferably from about 1 mol to about 3 mol, of sodium hydroxide. In this method, a preferred reaction temperature ranges from about $0°$ C. to about $150°$ C., more preferably from $0°$ C. to $100°$ C., most preferably from $30°$ C. to $85°$ C.

A third method for preparation of the compound according to the present invention comprises treating a compound having the formula (B) in an alcohol having the formula $R^2$—O—$R^1$—OH with sodium hydroxide or potassium hydroxide in the presence of sodium silicate ($Na_2O \cdot nSiO_2$ wherein n is from about 1 to about 5, preferably from about 1 to about 3). Sodium hydroxide is preferably used in this method. More particularly, 1 mol of a compound of the formula (A) and from about 10 g to about 1,000 g, preferably from about 10 g to about 500 g, more preferably from about 30 g to about 100 g, are suspended in from about 100 ml to about 50 l, preferably from about 300 ml to about 5 l, more preferably from about 400 ml to about 2 l, of an alcohol of the formula $R^2$—O—$R^1$—OH and then treated with from about 1 mol to about 50 mol, preferably from about 1 mol to about 10 mol, more preferably from about 1 mol to about 3 mol, of sodium hydroxide. In this method, a preferred reaction temperature ranges from about $0°$ C. to about $150°$ C., preferably from $0°$ C. to $100°$ C., more preferably from $30°$ C. to $85°$ C.

The reaction solution obtained in any one of the above-described methods is filtered to remove insoluble substances. The filtrate is poured into a poor solvent for the compound of the general formula (I) (for example, an alcohol solvent such as isopropyl alcohol, n-butanol, etc.; an aromatic solvent such as toluene, etc.; an ester solvent such as ethyl acetate, etc.) to crystallize the compound of the general formula (I). Conventional purification procedures such as recrystallization can be additionally conducted, if desired.

In addition, the compound of the general formula (I) can be obtained by sulfonation of a compound of the general formula p—($R^2$—O—$R^1$—O)—$C_6H_4$—$NO_2$ wherein $R^1$ and $R^2$ have the same meaning as described above in a manner similar to that described in *Chemical Abstracts*, supra. Further, it is possible to chlorosulfonylate the compound of the formula p—($R^2$—O—$R^1$—O)—$C_6H_4$—$NO_2$ using chlorosulfonic acid. In this case, it is believed that the compound is obtained through the sulfonic acid (M=H$^\oplus$ in the general formula (I)). L. F. Fieser, *Experiments in Organic Chemistry*, 3rd Ed., Chapter 26, D. C. Heath and Co. (1955) describes general methods for obtaining a sulfonyl chloride using chlorosulfonic acid. By applying these methods or refluxing with heating a sulfonyl chloride (2-alkoxyalkoxy-5-nitrobenzenesulfonyl chloride obtained by chlorination of a compound in which M=Na$^\oplus$ in the general formula (I) in the manner as described hereinafter in methanol, a methanol solution of the corresponding sulfonic acid (M=H$^\oplus$ in the general formula (I)) is obtained. By treating the compound thus-prepared with potassium acetate, calcium hydroxide, barium hydroxide or pyridine, etc., a compound in which M=K$^\oplus$, Ca$^\oplus\frac{1}{2}$, Ba$^\oplus\frac{1}{2}$ or $C_5H_6N^\oplus$, etc., in the general formula (I) is obtained, respectively. A calcium salt and a barium salt can also be prepared using the difference in solubility in water, etc., from that of the corresponding sodium salt.

Typical examples of the synthesis of the compounds according to the present invention are illustrated in detail below. Unless otherwise indicated, all parts, percents, ratios and the like are by weight.

EXAMPLE 1

Synthesis of Compound (I-A)

[Method 1]

To a solution of sodium 2-methoxyethylate prepared by adding 7.3 g of sodium hydride (14.6 g of a 50% suspension in liquid paraffin) to 300 ml of 2-methoxyethanol, was added 55 g of sodium 2-chloro-5-nitrobenzenesulfonate with stirring. The reaction mixture was heated at $80°$ to $85°$ C. on a water bath with stirring for 30 minutes. After filtering the mixture while hot, 1.5 liters of isopropyl alcohol was added to the filtrate to form crystals. The crystals thus-precipitated were recovered by filtration and washed with 100 ml of isopropyl alcohol. Yield: 59 g, Melting Point: $238°$ to $239°$ C. The infrared absorption spectrum of the compound obtained (KBr tablet method) is shown in FIG. 1.

[Method 2]

A mixture of 5.2 g of sodium 2-chloro-5-nitrobenzenesulfonate, 0.6 g of manganese dioxide, 15 ml of 2-methoxyethanol, 1 ml of water and 0.95 g of sodium hydroxide was stirred at $75°$ C. for 40 minutes. After cooling (to $25°$ C.), the insoluble materials were removed by filtration and the filtrate was poured into 100 ml of isopropyl alcohol. The crystals thus-precipitated were recovered by filtration to obtain 4.8 g of sodium 2-(2-methoxyethoxy)-5-nitrobenzenesulfonate. Melting Point: $238°$ to $239°$ C. The infrared absorption spectrum of this compound was the same as that of the compound obtained in Method 1 above.

[Method 3]

In the same manner as described in Method 2 above except that 0.8 g of sodium silicate ($Na_2O \cdot nSiO_2$ wherein n is about 3) was used in place of the manganese dioxide, 4.8 g of sodium 2-(2-methoxyethoxy)-5-nitrobenzenesulfonate was obtained. The same results were obtained using $Na_2O \cdot nSiO_2$ wherein n is about 1, about 2 and about 2.5, respectively. The infrared absorption spectrum of this compound was the same as that of the compound obtained in Method 1 above.

EXAMPLE 2

Synthesis of Compound (I-B)

Figure 2:
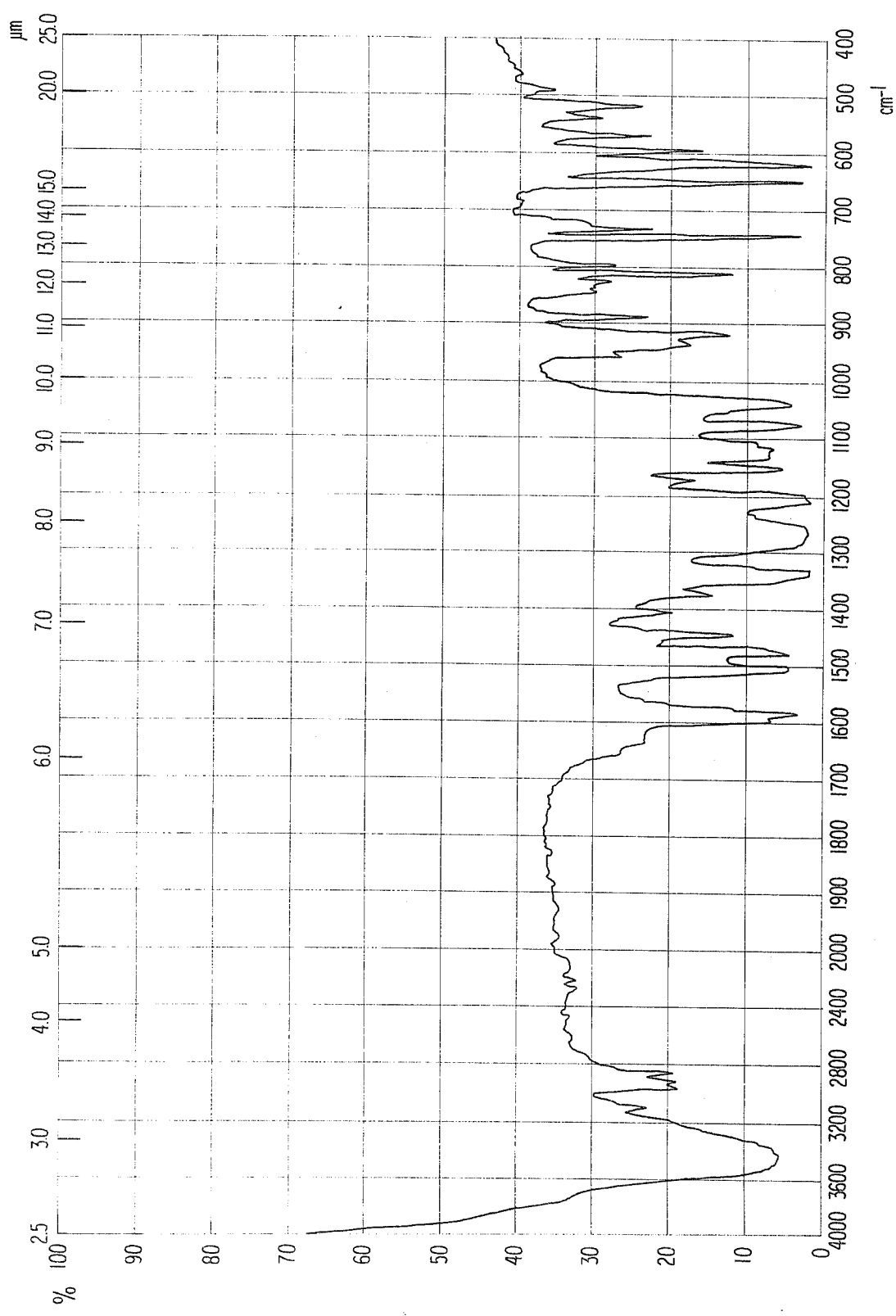

To a solution of sodium 2-ethoxyethylate prepared by adding 7.3 g of sodium hydride (14.6 g of a 50% suspension in liquid paraffin) to 300 ml 2-ethoxyethanol, was added 55 g of sodium 2-chloro-5-nitrobenzenesulfonate. The reaction mixture was heated at 80° to 85° C. with stirring for 30 minutes. After the completion of the reaction, the insoluble materials were removed by filtration and from the filtrate 150 ml of 2-ethoxyethanol was distilled off under reduced pressure. To the concentrated solution was added 300 ml of isopropyl alcohol and the mixture was cooled with ice (to 0° C.). The crystals thus-precipitated were recovered by filtration, washed with 100 ml of isopropyl alcohol and air-dried. Yield: 33 g; Melting Point: 248° to 249° C. The infrared absorption spectrum of this compound (KBr tablet method) is shown in FIG. 2.

Compound (I-B) was also obtained using 2-ethoxyethanol in place of 2-methoxyethanol in Method 2 or Method 3 of Example 1.

EXAMPLE 3

Synthesis of Compound (I-C)

Figure 3:
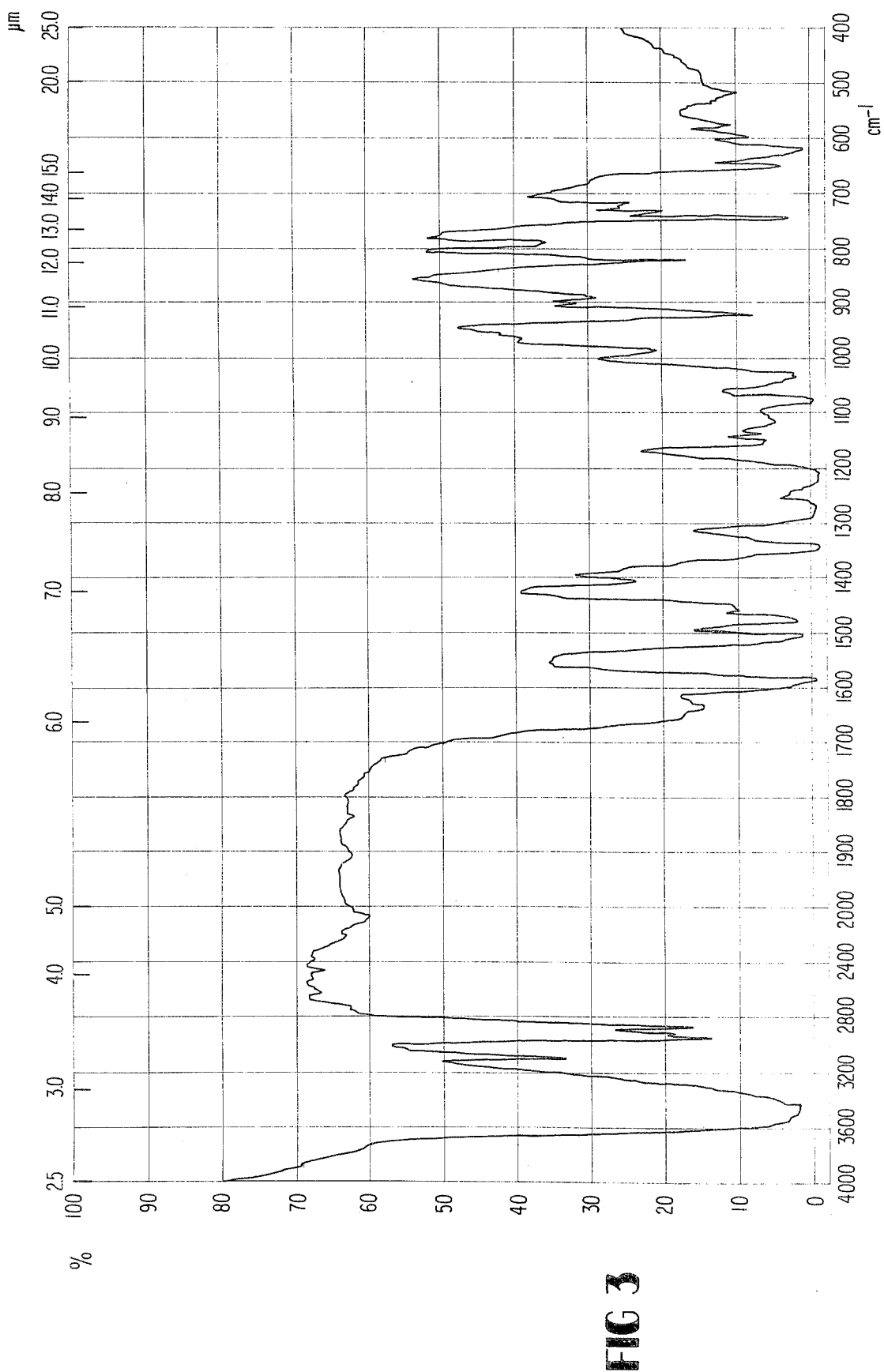

26.0 g of sodium 2-chloro-5-nitrobenzenesulfonate and 5.0 g of sodium silicate ($Na_2O \cdot nSiO_2$ wherein n is about 3) were suspended in 120 ml of 2-propoxyethanol. To the suspension was added dropwise with stirring a solution containing 5.0 g of sodium hydroxide dissolved in 5 ml of water at 65° C. for 10 minutes. After the completion of the addition, the reaction mixture was stirred at 65° C. for 3 hours and the insoluble materials were removed by filtration under suction. The solids which were deposited from the filtrate on standing were removed by filtration. The filtrate was concentrated to dryness and 100 ml of ethanol was added to the residue to form crystals. The crystals were recovered by filtration, washed with isopropyl alcohol and dried at 50° C. Yield: 14.1 g. The compound at first melted at 70° to 74° C., then solidified at about 130° C. and again melted at 206° to 209° C. The infrared absorption spectrum of the compound (KBr tablet method) is shown in FIG. 3.

EXAMPLE 4

Synthesis of Compound (I-E)

Figure 4:
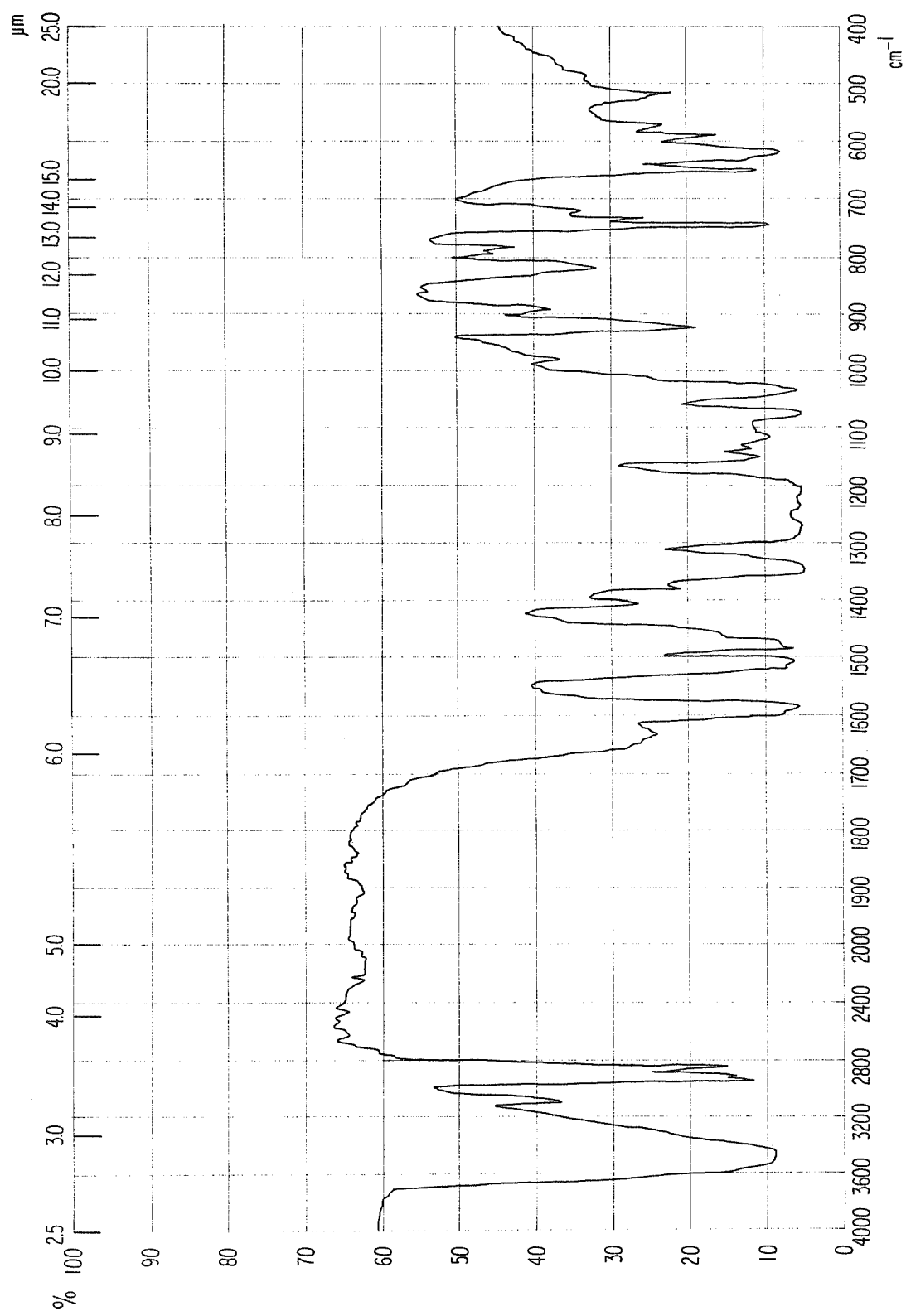

Compound (I-E) was obtained in the same manner as described in Method 2 of Example 1 except that ethylene glycol monobutyl ether was used in place of 2-methoxyethanol. Melting Point: 104° to 106° C. The infrared absorption spectrum of the compound (KBr tablet method) is shown in FIG. 4.

EXAMPLE 5

Synthesis of the Corresponding Calcium Salt of Compound (I-A)

29.9 g of Compound (I-A) obtained as described in Method 3 of Example 1 was dissolved in 70 ml of water with heating and to the solution was added 30 ml of an aqueous solution containing 8.0 g of calcium chloride. The solution was concentrated to dryness and 50 ml of 2-methoxyethanol was added to the residue. After removing the insoluble materials by filtration, 50 ml of toluene and 100 ml of isopropyl alcohol were added to the filtrate. The needle crystals thus-deposited were recovered by filtration, washed with isopropyl alcohol and dried at 100° C. Yield: 20.65 g; Melting Point: above 300° C.

EXAMPLE 6

Synthesis of the Corresponding Barium Salt of Compound (I-A)

29.9 g of Compound (I-A) obtained as described in Method 3 of Example 1 was dissolved in 170 ml of water and to the solution was added 50 ml of an aqueous solution containing 13.0 g of barium chloride dihydrate and the mixture was stirred for 1 hour. After removing the insoluble materials by filtration, the filtrate was allowed to stand in a refrigerator overnight. The needle crystals thus-deposited were recovered by filtration, washed with isopropyl alcohol and dried at 100° C. Yield: 14.6 g; Melting Point: above 300° C. From the elemental analysis (found, C: 30.46%, H: 3.12% and N: 4.01%; calculated for $C_{18}H_{20}N_2O_{14}S_2Ba$, C: 31.34%, H: 2.92% and N: (4.06%), the compound was estimated to have the following structure:

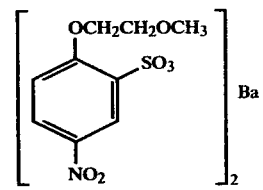

By using the compounds of the present invention as intermediates, dye releasing redox compounds which are suitable for use in the color diffusion transfer process can be prepared. Typical examples of the redox compounds which can be produced from the compounds of the present invention include compounds represented by the following general formula (II):

D—Redox Moiety   (II)

wherein D represents a dye moiety and Redox Moiety is a group represented by the following general formula (IIa):

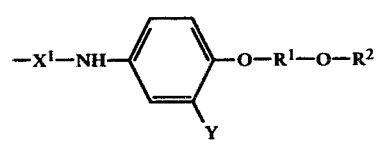

(IIa)

wherein $X^1$ represents an —$SO_2$— group or a —CO— group; Y represents an o- or p-hydroxyarylsulfamoyl group having a ballast group; and $R^1$ and $R^2$ each has the same meaning as defined in the general formula (I). Examples of these compounds of the general formula (II) wherein the Redox Moiety is a group represented by the general formula (IIa) above are disclosed in detail in copending U.S. Pat. Application Ser. No. 911,571 filed June 1, 1978, now abandoned, the disclosure of which is incorporated herein by reference.

Other redox compounds which can be prepared from the compounds of the present invention are those represented by the above-described general formula (II) wherein D represents a dye moiety and Redox Moiety is a group represented by the general formula (IIa) above in which Y in the moiety of the general formula (IIa) represents (a) a group of the formula:

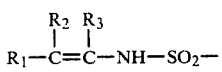

as described in the Japanese Patent Application (OPI) 104343/1976,
or (b) a group of the formula:

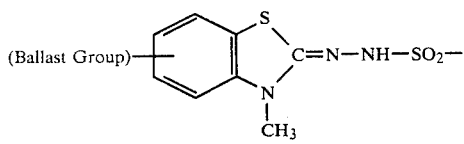

as described in U.S. Pat. No. 3,628,952, and disclosed by W. Rüschel in Society of Photographic Scientists and Engineers 1974 annual meeting.

In the above-described general formula (II), the dye releasing redox compound is characterized by the structure of the redox moiety, in particular, the presence of the —O—R¹—O—R² group. Due to the presence of the —O—R¹—O—R² group in the dye releasing redox compound, the light fastness of the transferred dye is improved, the transferability is improved and the advantages in preparation of the compound described hereinafter are attained, when the intermediate according to the present invention is used. In more detail, the improvement in transferability is based on the fact that the activity of the redox moiety is increased and consequently, the dye moiety is efficiently released from the dye-releasing redox compound due to the presence of the above-described —O—R¹—O—R² group.

Although the details of the reasons for the improvement in light fastness are still unclear, while not desiring to be bound, it is believed that it arises due to the association of the transferred dye, the steric conformation of the transferred dye and the affinity to a mordant of the transferred dye in an image receiving layer.

The dye-releasing redox compounds which can be obtained by using the compounds according to the present invention as intermediates are described in greater detail below.

In the general formula (II), an —SO₂— group is preferred for X¹.

The dye moiety represented by D includes a residue of a dye such as an azo dye, an azomethine dye, an indoaniline dye, an indophenol dye, an anthraquinone dye, a triarylmethane dye, an alizarin dye, a merocyanine dye, a nitro dye, a quinoline dye, a cyanine dye, an indigoid dye, a phthalocyanine dye, a metal complex dye, and the like.

An azo dye residue is particularly preferred for the dye moiety. Most particularly, an azo dye residue represented by the following formula (IIIa) or (IIIb) is preferred.

wherein A represents a coupling component residue (for example, a residue derived from a phenol or nucleus-substituted phenol, a 1- or 2-naphthol or a nucleus-substituted 1- or 2-naphthol, a pyrazolone or a nucleus-substituted pyrazolone, an acyclic or alicyclic β-diketone compound, etc.); and B represents a phenyl group or a nucleus-substituted phenyl group or a naphthyl group or a nucleus-substituted naphthyl group.

The term "coupling component" as used herein is well known in the dye art and means a compound capable of undergoing a coupling reaction with a diazonium compound. Coupling components are described in greater detail in Hiroshi Horiguchi, Sosetsu Gosei Senryo (Synthetic Dyes), pp. 110 to 112 and 124 to 129, Sankyo Publisher, Tokyo (1968); Yutaka Hosoda, Riron Seizo Senryo Kagaku (Theory of Manufactured Dye Chemistry), pp. 144 to 149, Gihodo Publisher, Tokyo (1957); the Society of Dyers and Colourists, Colour Index, 3rd Ed., Vol. 4, pp. 4009 to 4013; and H. A. Lubs, The Chemistry of Synthetic Dyes and Pigments, pp. 101 to 109, Waverly Press Inc., Baltimore (1955). In the present invention, a group A which is derived from a coupling component of the formula A-H is designated a coupling component residue. Of coupling components of the formula A-H, a phenol or a nucleus-substituted phenol, a 1- or 2-naphthol or a nucleus-substituted 1- or 2-naphthol, a pyrazolone or a nucleus-substituted pyrazolone, and an acyclic or alicyclic β-diketone compound are particularly preferred. The coupling position of these coupling components of the formula A-H is also well known in the dye art. In formula (IIIa) or (IIIb), the azo group (—N=N—) is bonded at the coupling position to A. For example, the coupling position in a phenol or a nucleus-substituted phenol is in the ortho or para position to the hydroxy group. The coupling position in a 1-naphthol or a nucleus-substituted 1-naphthol is in the 4- or 2-position, while the coupling position in a 2-naphthol or a nucleus-substituted 2-naphthol is in the 1-position. The coupling position in a pyrazolone or a nucleus-substituted pyrazolone is in the 4-position of the pyrazolone ring. The coupling position of an acyclic or alicyclic β-diketone compound is at the methylene group attached to both carbonyl groups (the so-called active methylene group). A phenyl group or a nucleus-substituted phenyl group is particularly preferred for B, since such a group advantageously influences the transferability of the released dye compound.

In one preferred embodiment, the dye residue of the formula (IIIb) is represented by the following formula (IV):

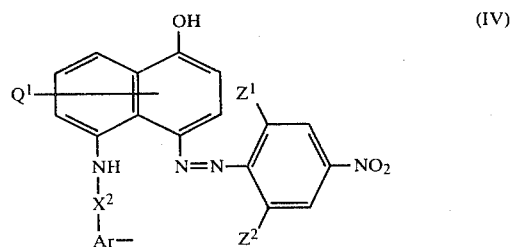

wherein Q¹, which can be present on either ring of the naphthol nucleus, represents a hydrogen atom, a halogen atom (e.g., a chlorine atom or a bromine atom), a sulfamoyl group represented by the formula —SO₂NR³R⁴, a group represented by the formula —SO₂R⁵, a carboxy group, a group represented by the formula —COOR⁶, or a group represented by the formula —CONR³R⁴, wherein in the above groups, R³ represents a hydrogen atom or a straight or branched chain alkyl group having 1 to 8 carbon atoms, which may be substituted, $R^4$ represents a hydrogen atom, or a straight or branched chain alkyl group having 1 to 8 carbon atoms, which may be substituted, a straight or branched chain aralkyl group having 7 to 12 carbon atoms or a phenyl group which may be substituted, and $R^3$ and $R^4$ may combine directly or through an oxygen atom to form a ring (preferably a 5- to 8-membered ring, for example, morpholino, piperidino, pyrrolidino, etc.), $R^5$ represents a straight or branched chain alkyl group having 1 to 8 carbon atoms, which may be substituted, or a straight or branched chain aralkyl group having 7 to 12 carbon atoms, and $R^6$ represents a straight or branched chain alkyl group having 1 to 8 carbon atoms or a phenyl group which may be substituted; $X^2$ represents $-SO_2-$ or $-CO-$; Ar represents a phenylene group which may be substituted; $Z^1$ represents a halogen atom (e.g., a chlorine atom or a bromine atom), a cyano group, a nitro group, a trifluoromethyl group, a straight or branched chain alkyl group having 1 to 8 carbon atoms, a straight or branched chain alkoxy group having 1 to 8 carbon atoms, a carboxylic acid ester group represented by the formula $-COOR^6$, a fluorosulfonyl group, a phenoxysulfonyl group which may be substituted, a sulfamoyl group represented by the formula $-SO_2NR^3R^4$, a carbamoyl group represented by the formula $-CONR^3R^4$, a straight or branched chain alkylsulfonyl group having 1 to 8 carbon atoms in which the alkyl moiety may be substituted, a phenylsulfonyl group which may be substituted, wherein, in the above groups, $R^3$, $R^4$ and $R^6$ each has the same meaning as defined above; $Z^2$ represents a hydrogen atom, a halogen atom (e.g., a chlorine atom or a bromine atom), a nitro group, a cyano group or a trifluoromethyl group.

In the sulfamoyl group represented by the formula $-SO_2NR^3R^4$ for $Q^1$, $R^3$ is preferably a hydrogen atom, an unsubstituted alkyl group having 1 to 4 carbon atoms (e.g., a methyl group, an ethyl group, a propyl group, an isopropyl group, a butyl group, a t-butyl group, etc.) or a substituted alkyl group having 1 to 4 carbon atoms in the alkyl moiety, and $R^4$ is preferably a hydrogen atom, an unsubstituted alkyl group having 1 to 4 carbon atoms (e.g., a methyl group, an ethyl group, a propyl group, an isopropyl group, a butyl group, a t-butyl group, etc.), a substituted alkyl group having 1 to 4 carbon atoms in the alkyl moiety, a benzyl group, an unsubstituted phenyl group, or a substituted phenyl group having 6 to 9 carbon atoms. Also, $R^3$ and $R^4$ may be combine directly or through an oxygen atom to form a 5- or 6-membered ring. In particular, (1) where $R^3$ and $R^4$ each represents a hydrogen atom and (2) where one of $R^3$ and $R^4$ represents a hydrogen atom and the other of $R^3$ and $R^4$ represents an alkyl group having 1 to 4 carbon atoms, are preferred because of easy availability of the starting materials and excellent transferability of the dye compound formed. The same situation exists for the $-CONR^3R^4$ group.

With respect to the $-SO_2R^5$ group, $R^5$ preferably represents an unsubstituted alkyl group having 1 to 4 carbon atoms (e.g., a methyl group, an ethyl group, a propyl group, an isopropyl group, a butyl group, a t-butyl group, etc.), a substituted alkyl group having 1 to 4 carbon atoms in the alkyl moiety or a benzyl group. In particular, an alkyl group having 1 to 4 carbon atoms and a benzyl group are preferred because of easy availability of the starting materials and excellent transferability of the dye compound formed. In case of the $-COOR^6$ group, $R^6$ preferably represents an unsubstituted alkyl group having 1 to 4 carbon atoms (e.g., a methyl group, an ethyl group, a propyl group, an isopropyl group, a butyl group, a t-butyl group, etc.), a substituted alkyl group having 1 to 4 carbon atoms in the alkyl moiety, an unsubstituted phenyl group or a substituted phenyl group having 6 to 9 carbon atoms.

Examples of suitable substituents which can be present in the above-described substituted alkyl groups represented by $R^3$ to $R^6$ include one or more of a cyano group, a straight or branched chain alkoxy group having 1 to 4 carbon atoms (e.g., a methoxy group, an ethoxy group, etc.), a hydroxy group, a carboxy group, a sulfo group, etc. Examples of suitable substituents which can be present in the above-described substituted phenyl group represented by $R^4$ or $R^6$ include one or more of a hydroxy group, a halogen atom (e.g., a chlorine atom or a bromine atom), a carboxy group, a sulfo group, a sulfamoyl group, etc.

Examples of suitable substituents which can be present in the above-described substituted phenylene group represented by Ar include one or more of a carboxy group, a halogen atom (e.g., a chlorine atom or a bromine atom), a straight or branched chain alkyl group having 1 to 4 carbon atoms (e.g., a methyl group, an ethyl group, a propyl group, an isopropyl group, a butyl group, a t-butyl group, etc.), a straight or branched chain alkoxy group having 1 to 4 carbon atoms (e.g., a methoxy group, an ethoxy group, a propoxy group, etc.), etc.

The alkyl group represented by $Z^1$ may be a straight chain or branched chain alkyl group and is preferably an alkyl group having 1 to 8 carbon atoms (more preferably 1 to 4 carbon atoms, e.g., a methyl group, an ethyl group, a propyl group, an isopropyl group, a butyl group, a t-butyl group, etc.). The alkoxy group represented by $Z^1$ may be a straight chain or branched chain alkoxy group and is preferably an alkoxy group having 1 to 8 carbon atoms (more preferably 1 to 4 carbon atoms, e.g., a methoxy group, an ethoxy group, a propoxy group, etc.).

Preferred examples of $-SO_2NR^3R^4$ and $-CONR^3R^4$ groups represented by $Z^1$ are the same as those described for $Q^1$ above.

The alkylsulfonyl group represented by $Z^1$ may be a straight chain or branched chain alkylsulfonyl group and is preferably an alkylsulfonyl group having 1 to 8 carbon atoms (more preferably 1 to 4 carbon atoms, e.g., a methylsulfonyl group, an ethylsulfonyl group, etc.). Examples of suitable substituents which can be present in the substituted alkylsulfonyl group (preferably having 1 to 8 carbon atoms, more preferably 1 to 4 carbon atoms in the alkyl moiety) represented by $Z^1$ include one or more of a cyano group, an alkoxy group having 1 to 4 carbon atoms (e.g., a methoxy group, an ethoxy group, a propoxy group, etc.), a hydroxy group, a carboxy group, a sulfo group, etc. Examples of suitable substituents which can be present in the substituted phenoxysulfonyl group and the substituted phenylsulfonyl group represented by $Z^1$ include one or more of a hydroxy group, a halogen atom (e.g., a chlorine atom or a bromine atom), a carboxy group, a sulfo group, a sulfamoyl group, etc.

In another preferred embodiment, the dye residue of the formula (IIIa) is represented by the following formula (V):

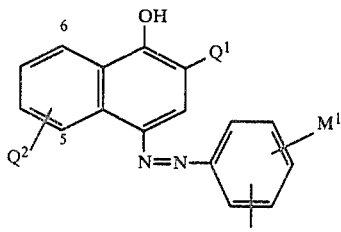

(V)

wherein $Q^1$ has the same meaning as defined in the formula (IV); $Q^2$, which is positioned at the 5- or the 8-position to the hydroxy group, represents a hydroxy group, an —NHCOR$^4$ group or an —NHSO$_2$R$^4$ group, wherein $R^4$ has the same meaning as defined in the formula (IV) except that $R^4$ is not a hydrogen atom; $M^1$ represents a hydrogen atom, a straight or branched chain alkyl group having 1 to 8 carbon atoms which may be substituted, a straight or branched chain alkoxy group having 1 to 8 carbon atoms or a halogen atom (e.g., a chlorine atom or a bromine atom).

The unsubstituted alkyl group represented by $M^1$ is preferably an unsubstituted alkyl group having 1 to 8 carbon atoms (more preferably 1 to 4 carbon atoms, e.g., a methyl group, an ethyl group, a propyl group, an isopropyl group, a butyl group, a t-butyl group, etc.). The substituted alkyl group represented by $M^1$ is a substituted alkyl group having 1 to 8 carbon atoms (more preferably 1 to 4 carbon atoms) in the alkyl moiety. Examples of suitable substituents which can be present in the substituted alkyl group are one or more of preferably those described above for the substituted alkyl group for $R^3$ to $R^6$. The alkoxy group represented by $M^1$ is preferably an alkoxy group having 1 to 8 carbon atoms (more preferably 1 to 4 carbon atoms, e.g., a methoxy group, an ethoxy group, a propoxy group, etc.).

In still another preferred embodiment, the dye residue of the formula (IIIa) is represented by the following formula (VI):

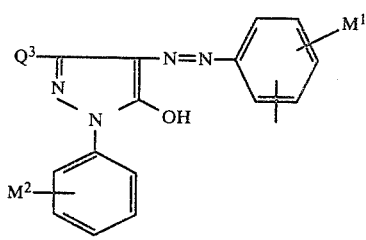

(VI)

wherein $M^1$ has the same meaning as defined in the formula (V); $M^2$ represents a hydrogen atom, a straight or branched chain alkyl group having 1 to 8 carbon atoms which may be substituted, a sulfamoyl group represented by the formula —SO$_2$NR$^3$R$^4$, wherein $R^3$ and $R^4$ each has the same meaning as defined in the formula (IV) above, or a group represented by the formula —COOR$^6$, wherein $R^6$ has the same meaning as defined in the formula (IV) above; and $Q^3$ represents a cyano group or a carbamoyl group represented by the formula —CONR$^3$R$^4$, wherein $R^3$ and $R^4$ each has the same meaning as defined in the formula (IV) above.

The unsubstituted alkyl group or the substituted alkyl group represented by $M^2$ is preferably an unsubstituted alkyl group having 1 to 4 carbon atoms (e.g., a methyl group, an ethyl group, a propyl group, an isopropyl group, a butyl group, a t-butyl group, etc.) or a substituted alkyl group having 1 to 4 carbon atoms in the alkyl moiety. Examples of suitable substituents which can be present in the substituted alkyl group are one or more of those as described above for the substituted alkyl group for $R^3$ to $R^6$.

Preferred sulfamoyl groups substituted with an o- or p-hydroxyaryl group having a ballast group bonded thereto represented by Y in the formula (II) are represented by the general formula (VII):

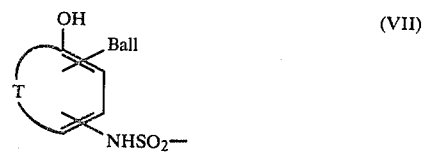

(VII)

wherein Ball represents a ballast group; T represents the carbon atoms necessary to complete a benzene ring, which may be unsubstituted or substituted, or a naphthalene ring, which may be unsubstituted or substituted; the —NHSO$_2$— group is present at the o- or p-position to the hydroxy group; and when T represents the atoms necessary to complete a naphthalene ring, Ball can be bonded to either of the two rings.

Examples of suitable substituents which can be present on the benzene ring or the naphthalene ring include, for example, one or more of a straight or branched chain alkyl group (preferably an alkyl group having 1 to 8 carbon atoms, and more preferably an alkyl group having 1 to 4 carbon atoms, e.g., a methyl group, an ethyl group, a propyl group, an isopropyl group, a butyl group, a t-butyl group, etc.) or a halogen atom (such as a chlorine atom, etc.).

The ballast group, Ball, is an organic ballast group capable of rendering the dye-releasing redox compound nondiffusible during development in an alkaline processing solution and preferably is or contains a hydrophobic residue having 8 to 32 carbon atoms. This organic ballast group can be bonded to the dye-releasing redox compound directly or through a linking group, for example, an imino bond, an ether bond, a thioether bond, a carbonamido bond, a sulfonamido bond, a ureido bond, an ester bond, an imido bond, a carbamoyl bond, a sulfamoyl bond, etc.

Specific examples of ballast groups are illustrated below:

an alkyl group or an alkenyl group (for example, a dodecyl group, an octadecyl group, etc.), an alkoxyalkyl group (for example, a 3-(octyloxy)propyl group, a 3-(2-ethyl-undecyloxy)propyl group, etc., as described in Japanese Patent Publication 27563/1964, etc.), an alkylaryl group (for example, a 4-nonylphenyl group, a 2,4-di-tert-butylphenyl group, etc.), an alkylaryloxyalkyl group (for example, a 2,4-di-tert-pentylphenoxymethyl group, an α-(2,4-di-tert-pentylphenoxy)propyl group, a 1-(3-pentadecylphenoxy)ethyl group, etc.), an acylamidoalkyl group (for example, a group described in U.S. Pat. Nos. 3,337,344 and 3,418,129, a 2-(N-butyl-hexadecanamido)ethyl group, etc.), an alkoxyaryl or aryloxyaryl group (for example, a 4-(n-octadecyloxy)-phenyl grup, a 4-(4-n-dodecylphenyloxy)phenyl group, etc.), a residue containing both an alkyl or alkenyl long-chain aliphatic group and a watersolubilizing group such as a carboxy group or a sulfo group (for example, a 1-carboxymethyl-2-nonadecenyl group, a 1-sulfoheptadecyl group, etc.), an alkyl group substituted with an ester group (for example, a 1-ethoxycarbonylheptadecyl group, a 2-(n-dodecyloxycarbonyl)ethyl group, etc.), an alkyl group substituted with an aryl group or a heterocyclic group (for example, a 2-[4-(3-methoxycarbonylheneicosanamido)phenyl]-ethyl group, a 2-[4-(2-n-octadecylsuccinimido)phenyl]ethyl group, etc.), and an aryl group substituted with an aryloxyalkoxycarbonyl group (for example, a 4-[2-(2,4-di-tert-pentylphenoxy)-2-methylpropyloxycarbonyl]phenyl group, etc.)

Of the above-described organic ballast groups, those bonded to a bridging group as represented by the following general formulae (VIII) to (IX) are particularly preferred.

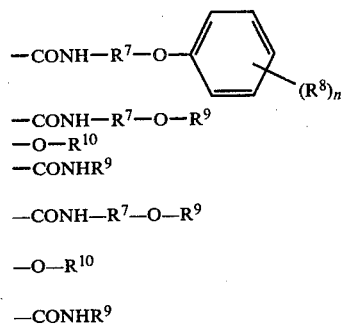

—CONH—$R^7$—O—$R^9$ (IX)

—O—$R^{10}$ (X)

—CONH$R^9$ (XI)

wherein $R^7$ represents a straight or branched chain alkylene group having 1 to 10 carbon atoms, preferably 1 to 6 carbon atoms (such as a propylene group, a butylene group, etc.); $R^8$ represents a hydrogen atom or a straight or branched chain alkyl group having 1 to 10 carbon atoms, preferably 1 to 6 carbon atoms (such as a tert-amyl group, etc.); n represents an integer of 1 to 5 (preferably 1 or 2); $R^9$ represents a straight or branched chain alkyl group having 4 to 30 carbon atoms, preferably 10 to 20 carbon atoms (such as a dodecyl group, a tetradecyl group, a hexadecyl group, etc.); and $R^{10}$ represents a straight or branched chain alkyl group having 8 to 30 carbon atoms, preferably 10 to 20 carbon atoms (such as a hexadecyl group, an octadecyl group, etc.) or a substituted alkyl group having 8 or more carbon atoms in which the alkyl moiety has 1 or more carbon atoms, with examples of suitable substituents being one or more of, for example, a carbamoyl group, etc.

Specific examples of the sulfamoyl groups represented by the formula (VII) are illustrated below:

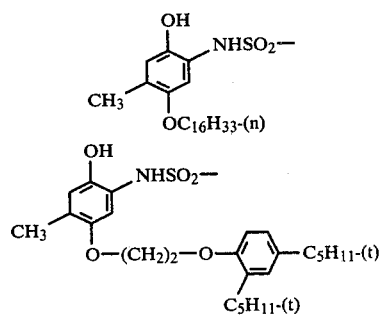

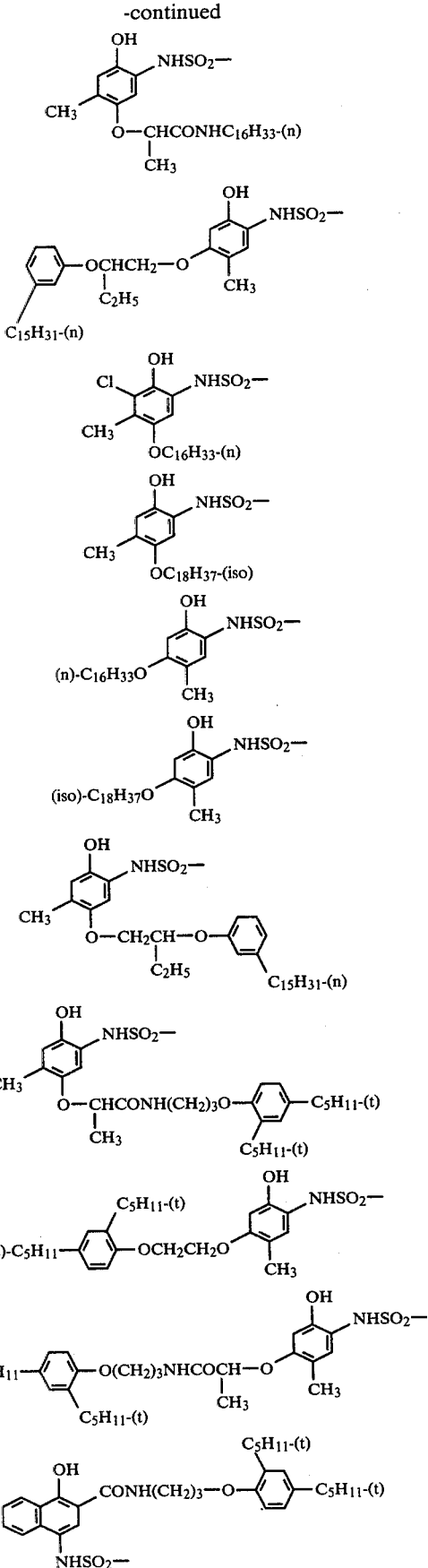

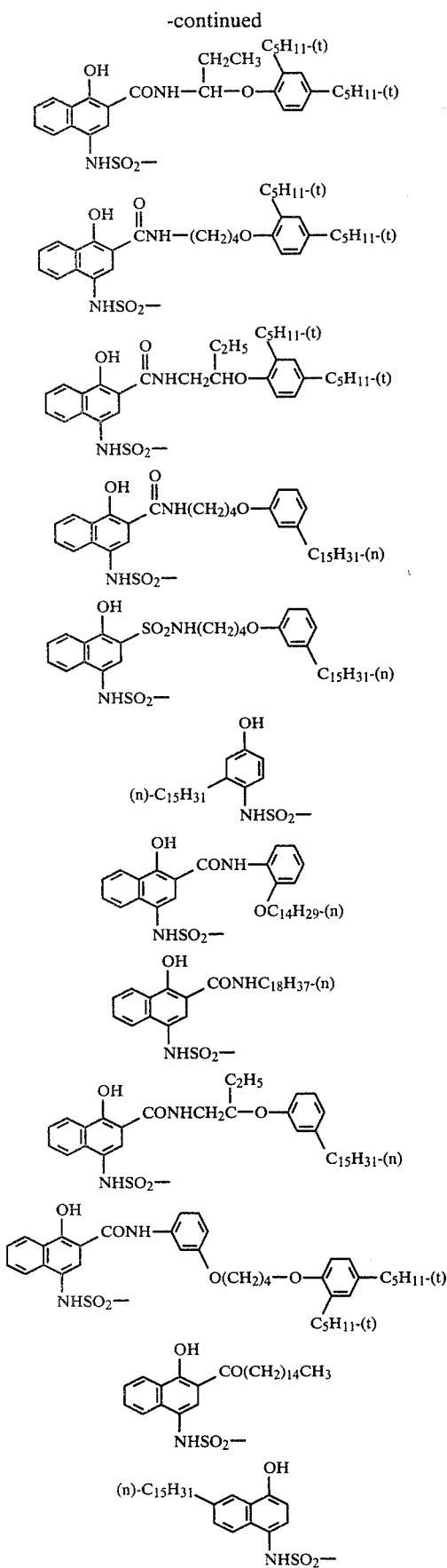

Furthermore, the groups described in *Research Disclosure*, Vol. 130, No. 13024 (February, 1975) and U.S. Pat. No. 4,053,312 are useful for Y.

A preferred compound obtained using the compound of the present invention is a compound having a dye moiety D represented by the formula (IV), and in which $R^1$ represents a —CH₂CH₂—group;

$R^2$ represents a straight chain or branched chain alkyl group having 1 to 4 carbon atoms (for example, a methyl group, an ethyl group, a propyl group, an isopropyl group, a butyl group, etc.);

$Q^1$, which is present at the 2-position with respect to the hydroxy group of the naphthalene ring, represents a hydrogen atom or a sulfamoyl group represented by the formula —SO₂NR³R⁴, wherein $R^3$ and $R^4$, which may be the same or different, each represents an unsubstituted alkyl group having 1 to 4 carbon atoms or a substituted alkyl group having 1 to 4 carbon atoms in the alkyl moiety, with examples of suitable substituents for the substituted alkyl group for $R^3$ and $R^4$ including a cyano group, an alkoxy group, a hydroxy group, a carboxy group, a sulfo group, etc., and also $R^3$ and $R^4$ can combine directly or through an oxygen atom to form a 5- or 6-membered ring;

$X^1$ and $X^2$ each represents an —SO₂—group;

Ar represents an m- or p-phenylene group;

Y represents a sulfamoyl group represented by the general formula (VII);

$Z^1$ represents a chlorine atom, a fluorine atom, a bromine atom, a cyano group, a nitro group, a trifluoromethyl group, a fluorosulfonyl group, a sulfamoyl group represented by the formula —SO₂NHR¹¹, wherein $R^{11}$ represents, preferably, an unsubstituted alkyl group having 1 to 4 carbon atoms or a substituted alkyl group having 1 to 4 carbon atoms in the alkyl moiety, with examples of suitable substituents in the substituted alkyl group including a cyano group, an alkoxy group, a hydroxy group, a carboxy group, a sulfo group, etc., an unsubstituted alkylsulfonyl group having 1 to 4 carbon atoms, a substituted alkylsulfonyl group having 1 to 4 carbon atoms in the alkyl moiety (with examples of suitable substituents including a cyano group, an alkoxy group, a hydroxy group, a carboxy group, a sulfo group, etc.), an unsubstituted phenylsulfonyl group, or a substituted phenylsulfonyl group (with examples of suitable substituents including a hydroxy group, a halogen atom, a carboxy group, a sulfo group, a sulfamoyl group, etc.); and $Z^2$ represents a hydrogen atom, a chlorine atom, a bromine atom or a fluorine atom.

A particularly preferred compound obtained using the compound of the present invention is a compound having a dye moiety D represented by the formula (IV), and in which $R^1$ represents a —$CH_2CH_2$— group;

$R^2$ represents a straight chain or branched chain alkyl group having 1 to 4 carbon atoms (e.g., a methyl group, an ethyl group, a propyl group, an isopropyl group, a butyl group, etc.);

$Q^1$ represents a hydrogen atom;

$X^1$ and $X^2$ each represents an —$SO_2$— group;

Ar represents an m-phenylene group;

Y represents a sulfamoyl group represented by the general formula (VII);

$Z^1$ represents a chlorine atom, a bromine atom, a cyano group, a trifluoromethyl group, a nitro group or an alkylsulfonyl group having 1 to 4 carbon atoms (e.g., a methylsulfonyl group, an ethylsulfonyl group, etc.); and $Z^2$ represents a hydrogen atom, a chlorine atom or a bromine atom.

Another preferred compound obtained using the compound of the present invention is a compound having a dye moiety D represented by the formula (V), and in which $R^1$ represents a —$CH_2CH_2$— group;

$R^2$ represents a straight chain or branched chain alkyl group having 1 to 4 carbon atoms (for example, a methyl group, an ethyl group, a propyl group, an isopropyl group, a butyl group, etc.);

$X^1$ represents an —$SO_2$- group;

$Q^1$ represents a hydrogen atom or a sulfamoyl group represented by the formula —$SO_2NR^3R^4$, wherein $R^3$ and $R^4$, which may be the same or different, each represents an unsubstituted alkyl group having 1 to 4 carbon atoms or a substituted alkyl group having 1 to 4 carbon atoms in the alkyl moiety, with examples of suitable substituents in the substituted alkyl group including a cyano group, an alkoxy group, a hydroxy group, a carboxy group, a sulfo group, etc., and also $R^3$ and $R^4$ can combine directly or through an oxygen atom to form a 5- or 6-membered ring;

$Q^2$ represents a hydroxy group or an —$NHSO_2R^4$ group, wherein $R^4$ has the same meaning as defined above, except that $R^4$ is not a hydrogen atom, at the 5-position;

$M^1$ represents a hydrogen atom, an unsubstituted alkyl group having 1 to 4 carbon atoms, an alkoxy group having 1 to 4 carbon atoms or a chlorine atom; and Y represents a sulfamoyl group represented by the general formula (VII).

Another particularly preferred compound obtained using the compound of the present invention is a compound having a dye moiety D represented by the formula (V), and in which $R^1$ represents a —$CH_2CH_2$—group;

$R^2$ represents a straight chain or branched chain unsubstituted alkyl group having 1 to 4 carbon atoms (for example, a methyl group, an ethyl group, an n-propyl group, an isopropyl group, an n-butyl group, etc.);

$Q^1$ represents a group of the formula

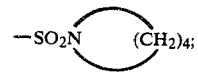

$Q^2$ represents an —$NHSO_2$—alkyl group (with the alkyl group having 1 to 4 carbon atoms) at the 5-position;

$M^1$ represents a methyl group or a hydrogen atom; and

Y represents a sulfamoyl group represented by the general formula (VII).

A still further preferred compound obtained using the compound of the present invention is a compound having a dye moiety D represented by the formula (VI), and in which $R^1$ represents a —$CH_2CH_2$—group;

$R^2$ represents a straight chain or branched chain unsubstituted alkyl group having 1 to 4 carbon atoms (for example, a methyl group, an ethyl group, an n-propyl group, an isopropyl group, an n-butyl group, etc.);

$X^1$ represents an —$SO_2$—group;

$M^1$ represents a hydrogen atom, an unsubstituted alkyl group having 1 to 4 carbon atoms, an alkoxy group having 1 to 4 carbon atoms or a halogen atom;

$M^2$ represents a hydrogen atom or an unsubstituted alkyl group having 1 to 4 carbon atoms;

$Q^3$ represents a cyano group or a —$CONR^3R^4$ group, wherein $R^3$ and $R^4$, which may be the same or different, each represents a hydrogen atom, an unsubstituted alkyl group having 1 to 4 carbon atoms or a substituted alkyl group having 1 to 4 carbon atoms in the alkyl moiety, with examples of suitable substituents in the substituted alkyl group including a cyano group, an alkoxy group, a hydroxy group, a carboxy group, a sulfo group, etc., and also $R^3$ and $R^4$ can combine directly or through an oxygen atom to form a 5- or 6-membered ring; and Y represents a sulfamoyl group represented by the general formula (VII).

Still another particularly preferred compound obtained using the compound of the present invention is a compound having a dye moiety D represented by the formula (VI), and in which $R^1$ represents a —$CH_2CH_2$— groups;

$R^2$ represents a straight chain or branched chain unsubstituted alkyl group having 1 to 4 carbon atoms (for example, a methyl group, an ethyl group, an n-propyl group, an isopropyl group, an n-butyl group, etc.);

$X^1$ represents an —$SO_2$— group;

$M^1$ represents a hydrogen atom, an unsubstituted alkyl group having 1 to 4 carbon atoms, an alkoxy group having 1 to 4 carbon atoms or a chlorine atom;

$M^2$ represents a hydrogen atom or an unsubstituted alkyl group having 1 to 4 carbon atoms;

$Q^3$ represents a cyano group; and

Y represents a sulfamoyl group represented by the general formula (VII).

Furthermore, of the above-described compounds, compounds in which Y is an o-hydroxyphenylsulfamoyl group having a ballast group bonded thereto or a nucleus-substituted o-hydroxyphenylsulfamoyl group having a ballast group bonded thereto are excellent. Particularly, compounds in which Y is an o-hydroxyphenylsulfamoyl group having an alkyl group (having 7 or less carbons atoms, preferably 1 to 2 carbon atoms) at the meta position to the hydroxy group in addition to a ballast group are preferred.

Specific examples of dye-releasing redox compounds which can be prepared from the compounds according to the present invention as intermediates are illustrated below:

Compound (1)

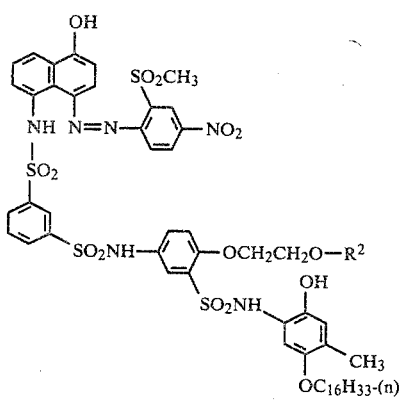

wherein $R^2$ is $CH_3$

Compound (2)

$R^2$ is $C_2H_5$ in the formula of Compound (1)

Compound (3)

$R^2$ is (n)—$C_4H_9$ in the formula of Compound (1)

Compound (4)

$R^2$ is (iso)—$C_3H_7$ in the formula of Compound (1)

Compound (5)

$R^2$ is (n)—$C_3H_7$ in the formula of Compound (1)

Compound (6)

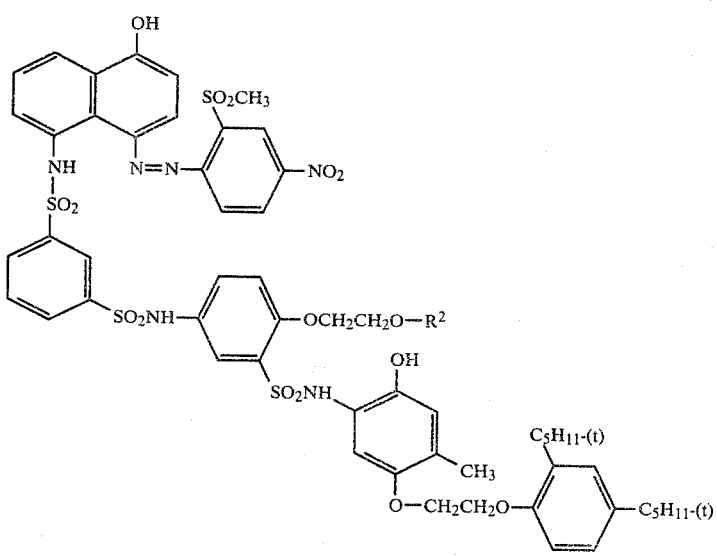

wherein $R^2$ is $CH_3$

Compound (7)

$R^2$ is $C_2H_5$ in the formula of Compound (6)

Compound (8)

$R^2$ is (n)—$C_4H_9$ in the formula of Compound (6)

Compound (9)

$R^2$ is (iso)—$C_3H_7$ in the formula of Compound (6)

Compound (10)

$R^2$ is (n)—$C_3H_7$ in the formula of Compound (6)

Compound (11)

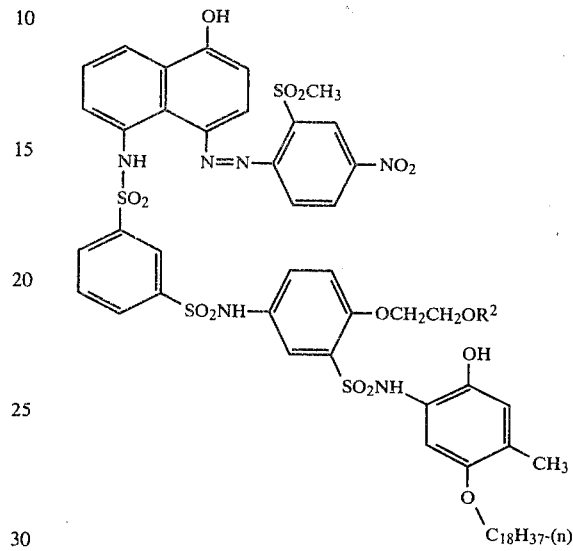

wherein $R^2$ is $CH_3$

Compound (12)

$R^2$ is $C_2H_5$ in the formula of Compound (11)

Compound (13)

$R^2$ is (n)—$C_4H_9$ in the formula of Compound (11)

Compound (14)

$R^2$ is (iso)—$C_3H_7$ in the formula of Compound (11)

Compound (15)

$R^2$ is (n)—$C_3H_7$ in the formula of Compound (11)

Compound (16)

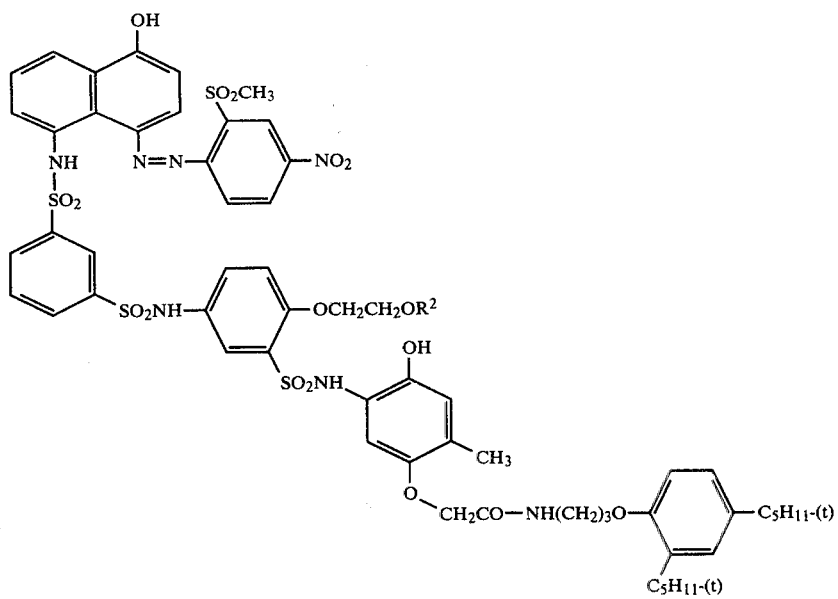
wherein R² is CH₃
Compound (17)
R² is C₂H₅ in the formula of Compound (16)
Compound (18)
R² is (n)—C₄H₉ in the formula of Compound (16)
Compound (19)
R² is (iso)—C₃H₇ in the formula of Compound (16)
Compound (20)
R² is (n)—C₃H₇ in the formula of Compound (16)
Compound (21)
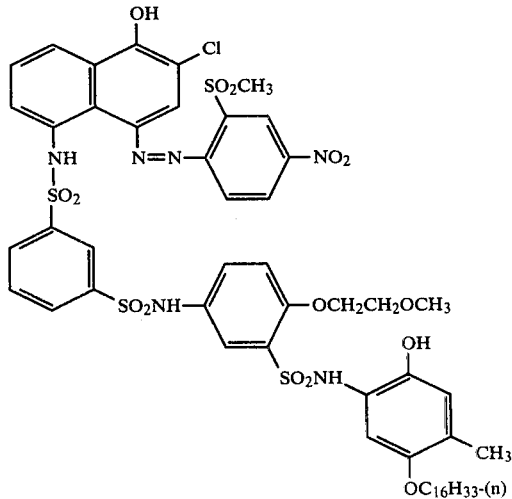
Compound (22)
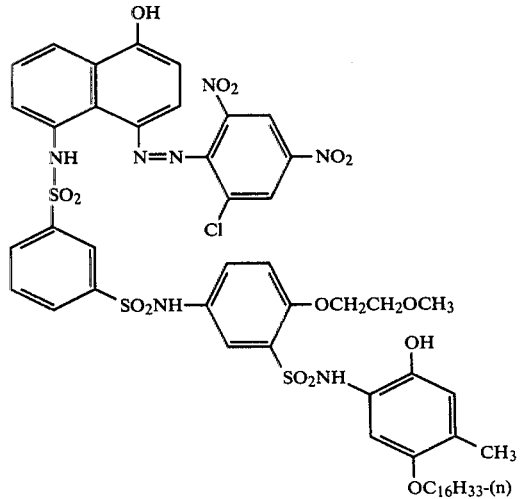

Compound (23)
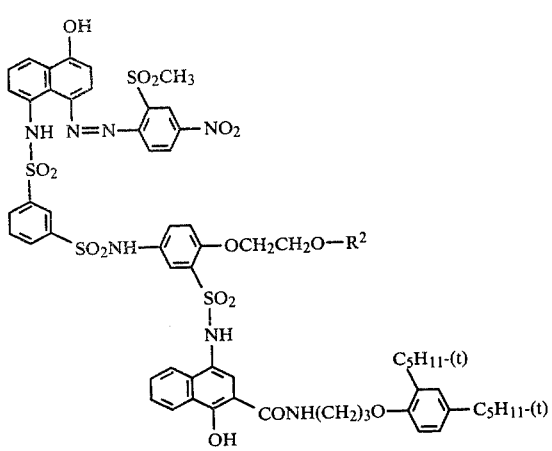
wherein R² is CH₃
Compound (24)
R² is C₂H₅ in the formula of Compound (23)
Compound (25)
R² is (n)—C₄H₉ in the formula of Compound (23)
Compound (26)
R² is (iso)—C₃H₇ in the formula of Compound (23)
Compound (27)
R² is (n)—C₃H₇ in the formula of Compound (23)
Compound (28)
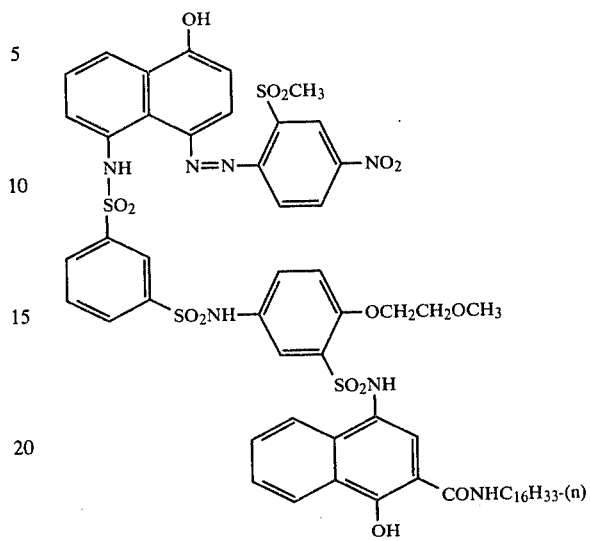
Compound (29)
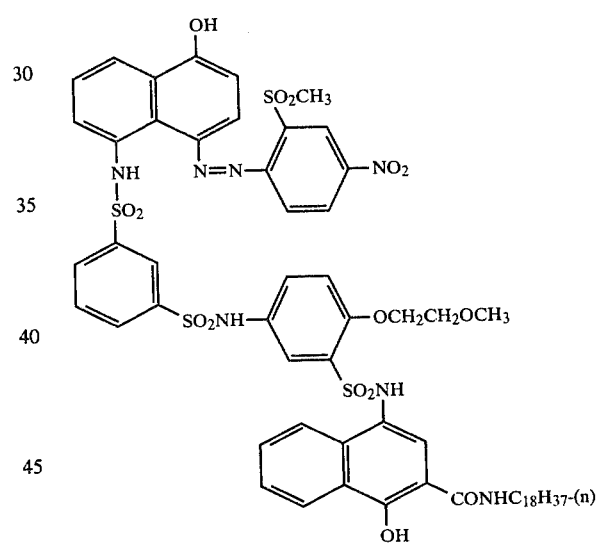
Compound (30)
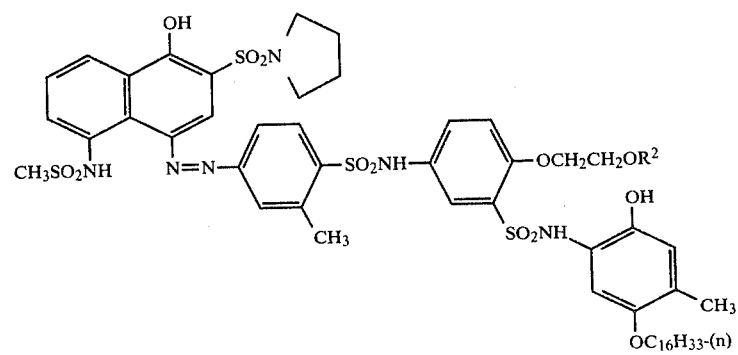
wherein R² is CH₃

Compound (31)

Compound (37)

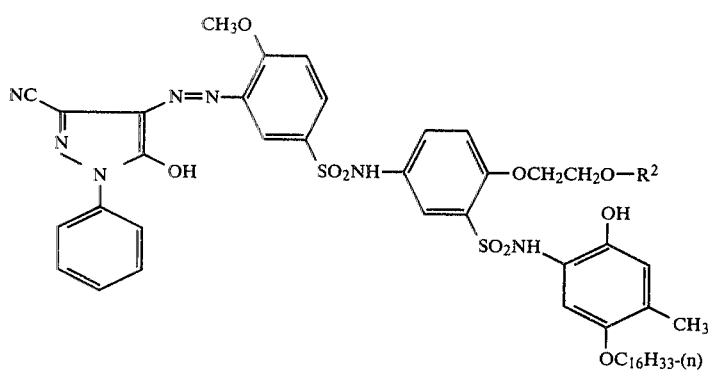

wherein $R^2$ is $CH_3$

Compound (38)

$R^2$ is $C_2H_5$ in the formula of Compound (30)

Compound (32)

$R^2$ is $C_2H_5$ in the formula of Compound (37)

Compound (39)

$R^2$ is (n)—$C_4H_9$ in the formula of Compound (30)

Compound (33)

$R^2$ is (n)—$C_4H_9$ in the formula of Compound (37)

Compound (40)

$R^2$ is (iso)—$C_3H_7$ in the formula of Compound (30)

Compound (34)

$R^2$ is (iso)—$C_3H_7$ in the formula of Compound (37)

Compound (41)

$R^2$ is (n)—$C_3H_7$ in the formula of Compound (30)

Compound (35)

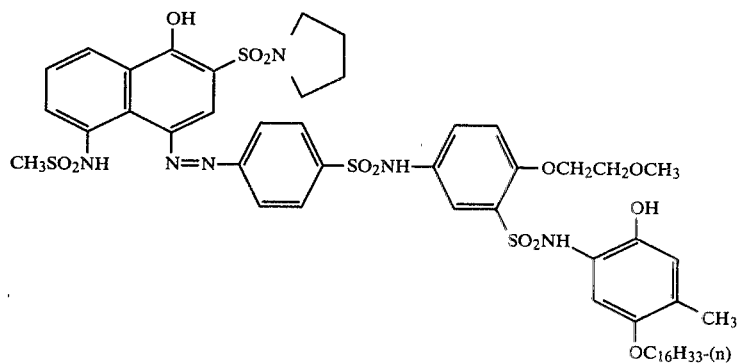

Compound (36)

$R^2$ is (n)—$C_3H_7$ in the formula of Compound (37)

Compound (42)

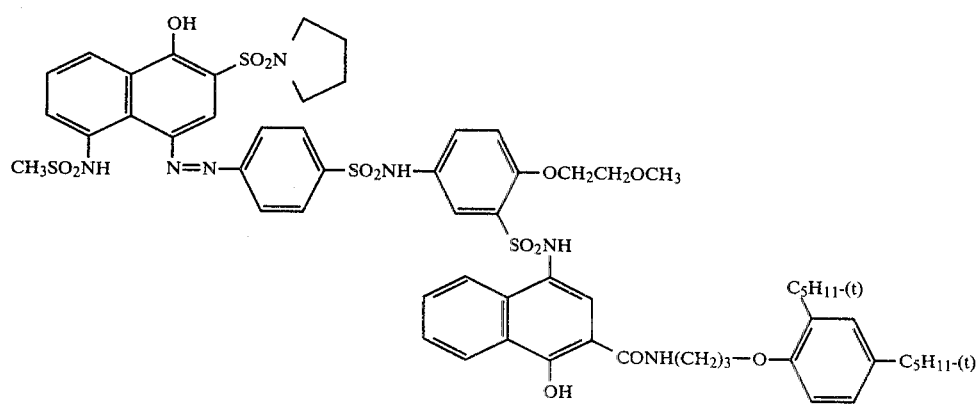

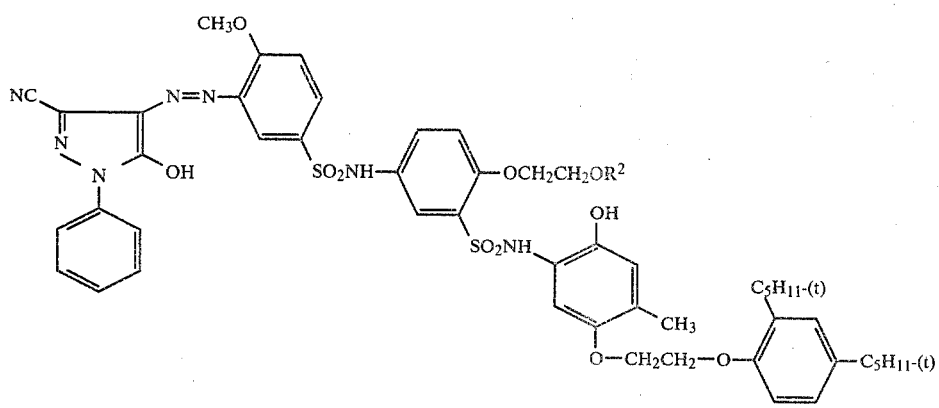

wherein R² is CH₃

Compound (43)

R² is C₂H₅ in the formula of Compound (42)

Compound (44)

R² is (n)—C₄H₉ in the formula of Compound (42)

Compound (45)

R² is (iso)—C₃H₇ in the formula of Compound (42)

Compound (46)

R² is (n)—C₃H₇ in the formula of Compound (42)

Compound (47)

wherein R² is CH₃

Compound (48)

R² is C₂H₅ in the formula of Compound (47)

Compound (49)

R² is (n)—C₄H₉ in the formula of Compound (47)

Compound (50)

R² is (iso)—C₃H₇ in the formula of Compound (47)

Compound (51)

R² is (n)—C₃H₇ in the formula of Compound (47)

Compound (52)

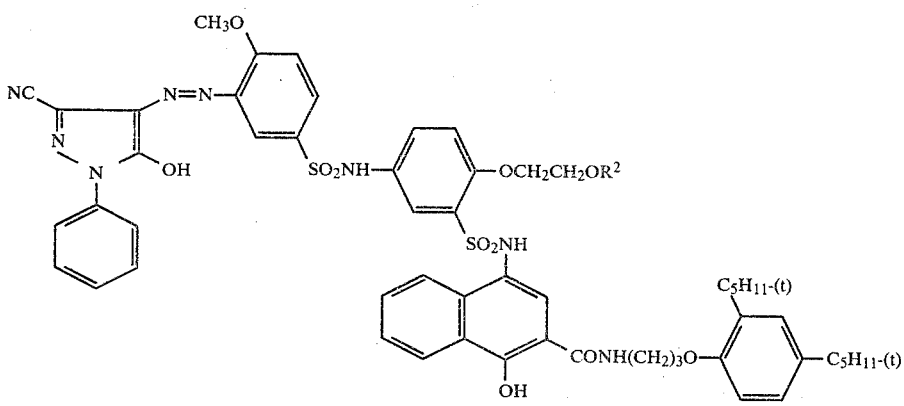

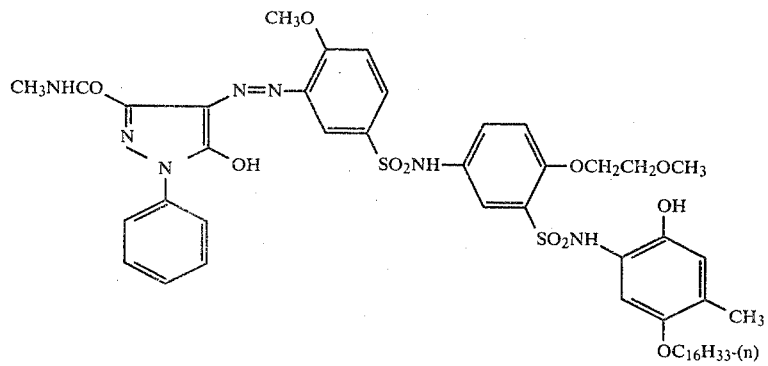

Compound (53)

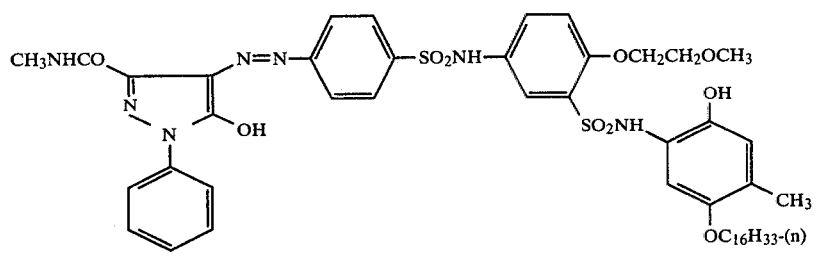

The synthesis steps for obtaining a compound having the formula (II) wherein $X^1$ is $SO_2$ from a compound having the formula (I) are schematically illustrated below:

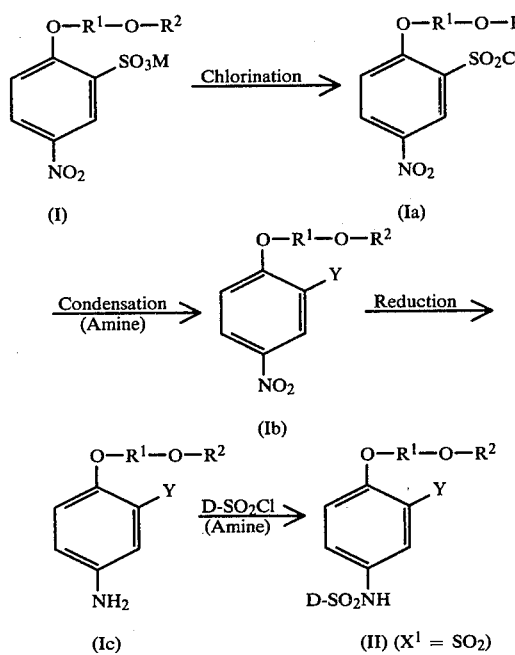

wherein $R^1$, $R^2$, Y and D each has the same meaning as defined in the formula (II).

In order to convert a compound of the formula (I) to a compound of the formula (Ia), a chlorinating agent such as phosphorus oxychloride (POCl₃), thionyl chloride (SOCl₂) or phosphorus pentachloride (PCl₅) is preferably used.

The chlorination reaction is preferably carried out in the presence of N,N-dimethylacetamide, N,N-dimethylformamide, N-methylpyrrolidone, etc. A compound of the formula (Ib) is obtained by a condensation of a sulfonyl chloride represented by the formula (Ia) and an o- or p-hydroxyarylamine having a ballast group. In general, the condensation reaction is preferably carried out in the presence of a basic compound (which acts as an acid removing agent). Examples of suitable basic compounds which can be used include a hydroxide of an alkali metal or an alkaline earth metal (for example, sodium hydroxide, potassium hydroxide, barium hydroxide, calcium hydroxide, etc.), an aliphatic amine (for example, triethylamine, etc.), an aromatic amine (for example, N,N-diethylaniline, etc.), a heteroaromatic amine (for example, pyridine, quinoline, α-, β- or γ-picoline, lutidine, collidine, 4-(N,N-dimethylamino)pyridine, etc.), or a heterocyclic base (for example, 1,5-diazabicyclo[4,3,0]nonene-5, 1,8-diazabicyclo[5,4,0]undecene-7, etc.). Of the above-described compounds, a heteroaromatic amine, particularly, pyridine, is preferably used as an acid removing agent.

Typical examples of reduction reactions for obtaining a compound of the formula (Ic) include a catalytic hydrogenation (e.g., using Raney nickel, palladium-carbon or charcoal as a catalyst), a reduction with iron powder, a reduction with hydrazine, etc. It should be emphasized that, in the compound of the formula (Ic), the basicity of the amino group is increased due to the presence of the $R^2$—O—$R^1$—O— group. Accordingly, the following condensation reaction of the compound of the formula (Ic) with a sulfonyl halide having the formula D—SO₂Cl proceeds easily. The condensation reaction of a compound represented by the formula (Ic) and a compound of the formula D—SO₂Cl is preferably carried out in the presence of a basic compound (which acts as an acid removing agent), e.g., as described above for the conversion of a compound of the formula (Ia) to a compound of the formula (Ib).

A specific example of the synthesis of a compound represented by the formula (II) from a compound represented by the formula (I) according to the present invention is illustrated below.

Reference Synthesis Example 1

Synthesis of Compound (1)

(a) Synthesis of 2-(2-Methoxyethoxy)-5-nitrobenzenesulfonyl Chloride 59 g of sodium 2-(2-methoxyethoxy)-5-nitrobenzenesulfonate prepared as described in Example 1 above was added to a mixture of 200 ml of acetone and 75 ml of phosphorus oxychloride. 75 ml of N,N-dimethylacetamide was added dropwise to the mixture with stirring while the reaction mixture was maintained at 30° to 40° C. After the completion of the addition, the mixture was allowed to stand with stirring until it cooled to room temperature (25° C.). The reaction mixture was then poured into 600 ml of ice water (0° C.), stirred for 30 minutes and the crystals thus-precipitated were recovered by filtration. The crystals were washed with water and air-dried. Yield: 56 g; Melting Point: 74° to 74.5° C.

(b) Synthesis of 2-[2'-(2-Methoxyethoxy)-5'-nitrobenzenesulfonamido]-4-hexadecyloxy-5-methylphenol 20 g of 2-amino-4-hexadecyloxy-5-methylphenol hydrochloride and 18 g of 4-(2-methoxyethoxy)nitrobenzene-3-sulfonyl chloride prepared as described in Step (a) above were added to a mixture of 100 ml of tetrahydrofuran and 10 ml of pyridine and the mixture was stirred at room temperature for 3 hours. The reaction mixture was added to a mixture of 300 ml of ice water and 50 ml of concentrated hydrochloric acid (35 wt%) with stirring. The crystals thus-precipitated were recovered by filtration, washed with water, air-dried and recrystallized from 100 ml of acetonitrile. Yield: 35 g; Melting Point: 85.5° to 86° C.

(c) Synthesis of 2-[2'-(2-Methoxyethoxy)-5'-aminobenzenesulfonamido]-4-hexadecyloxy-5-methylphenol 32 g of 2-[2'-(2-methoxyethoxy)-5'-nitrobenzenesulfonamido]-4-hexadecyloxy-5-methylphenol prepared as described in Step (b) above, 24 g of iron powder ($Fe_2O_3$), 12 g of $Fe_3O_4$, 0.6 g of ammonium chloride and 25 ml of water were added to 300 ml of isopropyl alcohol and the mixture was refluxed on a steam bath with stirring for 1 hour. After completion of the reaction, the mixture was filtered while hot and the filtrate was cooled with ice. The crystals thus-precipitated were recovered by filtration, washed with 50 ml of isopropyl alcohol and air-dried. Yield: 23 g; Melting Point: 142° to 144° C.

(d) Synthesis of 5-(3-Chlorosulfonylbenzenesulfonamido)-1-naphthol

To a stirred mixture of 2.1 g of 5-amino-1-naphthol (1/2 $H_2SO_4$ salt), 4.2 g of benzene-1,3-disulfonyl chloride, 10 ml of acetonitrile and 30 ml of methanol was added portionwise 3.4 g of sodium hydrogen carbonate at a temperature of 0° to 5° C. The mixture was stirred for 1 hour at 0° to 5° C. and poured into 300 ml of a 3% hydrochloric acid aqueous solution. The precipitated crude product was collected by filtration and recrystallized from benzene-ethyl acetate (1:1 by volume) to produce 2.9 g of the title compound.

(e) Synthesis of 4-(2-Methylsulfonyl-4-nitrophenylazo)-5-(3-chlorosulfonylbenzenesulfonamido)-1-naphthol 2-Methanesulfonyl-4-nitroaniline (50 m mol) was diazotized as described in J. B. Dickey, et al., Ind. Eng. Chem., 45, 1730 (1953). The solution of the diazonium salt was added to the cooled methanolic solution (200 ml) of 20.0 g of 5-(3-chlorosulfonylbenzenesulfonamido)-1-naphthol prepared as described in Step (d) above. After stirring for 1 hour, the precipitated product was collected by filtration, washed successively with methanol and with water, dried in air at room temperature (20°-25° C.). Yield: 36.5 g. The product was used in Step (f) below without further purification.

(f) Synthesis of Compound (1)

11 g of 2-[2'-(2-methoxyethoxy)-5'-aminobenzenesulfonamido]-4-hexadecyloxy-5-methylphenol prepared as described in Step (c) above and 12 g of 4-(2-methylsulfonyl-4-nitrophenylazo)-5-(3-chlorosulfonylbenzenesulfonamido)-1-naphthol prepared as described in Step (e) above were added to 80 ml of N,N-dimethylacetamide at 0° to 5° C. and 15 ml of pyridine was added thereto. The reaction solution was maintained at 0° to 5° C. and stirred for 2 hours. After completion of the reaction, the reaction mixture was added to a mixture of 350 ml of ice water and 50 ml of a 35% hydrochloric acid aqueous solution. The crystals thus-precipitated were recovered by filtration, washed with 500 ml of water and air-dried. The crystals were treated with activated carbon and recrystallized from isopropyl alcohol. Yield: 12 g; Melting Point: 130° to 134° C.; $\lambda$max in methyl Cellosolve containing 2% of a 0.1 N sodium hydroxide aqueous solution: 634 nm ($\epsilon = 9.52 \times 10^4$)

Syntheses using the compounds of the present invention to produce other dye-releasing redox compounds useful in the diffusion transfer photograhic process are described in detail in copending Application Ser. No. 911,571, filed June 1, 1978, the disclosure of which is incorporated herein by reference.

As set forth above, the compounds of this invention are useful in producing dye-releasing redox compounds, useful in the diffusion transfer process. Examples of dye-releasing redox compounds used in the diffusion transfer photographic process and diffusion transfer photographic film units are set forth in detail in the above-described copending Application Ser. No. 911,571, the disclosure of which is incorporated herein by reference.

Examples of the use of dye-releasing redox couplers in diffusion transfer photography are set forth below.

REFERENCE EXAMPLE 1

On a transparent polyethylene terephthalate film support were coated the layers described below in the order listed to prepare an integral type of multilayer multicolor light-sensitive film unit.

(1) An image-receiving layer containing 3.0 g/m$^2$ of copoly[styrene-N-vinylbenzyldimethyl-p-chlorobenzylammonium chloride] and 3.0 g/m$^2$ of gelatin.

(2) A white reflecting layer containing 22 g/m$^2$ of titanium dioxide and 2.2 g/m$^2$ of gelatin.

(3) An opaque layer containing 2.7 g/m$^2$ of carbon black and 2.7 g/m$^2$ of gelatin.

(4) A layer containing 0.65 g/m$^2$ of Compound (1) obtained from the intermediate of this invention (cyan dye-releasing redox compound), 0.3 g/m$^2$ of N,N-diethyllaurylamide and 1.1 g/m$^2$ of gelatin.

(5) A layer containing a red-sensitive internal latent image type silver iodobromide emulsion (containing 2 mol% of silver iodide, 1.1 g/m$^2$ of gelatin and 1.4 g/m$^2$ of silver), 0.022 g/m$^2$ of 2-methyl-3-(2-formylethyl)benzothiazolium bromide and 0.06 g/m$^2$ of 2,5-di-tert-octylhydroquinone.

(6) A layer containing 1.8 g/m$^2$ of gelatin and 0.8 g/m$^2$ of 2,5-di-tert-octylhydroquinone.

(7) A layer containing 0.80 g/m$^2$ of a known magenta dye-releasing redox compound of the structural formula:

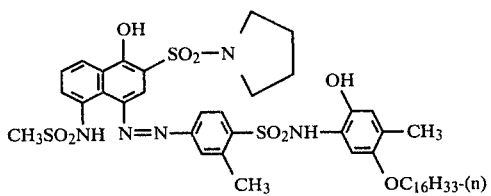

1.3 g/m$^2$ of N,N-diethyllaurylamide and 1.5 g/m$^2$ of gelatin.

(8) A layer containing a green-sensitive internal latent image type silver iodobromide emulsion (containing 2 mol% of silver iodide, 1.1 g/m$^2$ of gelatin and 1.4 g/m$^2$ of silver), 0.03 g/m$^2$ of 2,5-di-tert-octylhydroquinone and 0.019 g/m$^2$ of 2-methyl-3-(2-formylethyl)benzothiazolium bromide.

(9) A layer containing 1.5 g/m² of gelatin and 0.6 g/m² of 2,5-di-tert-octylhydroquinone.

(10) A layer containing 1.0 g/m² of a known yellow dye-releasing redox compound of the structural formula:

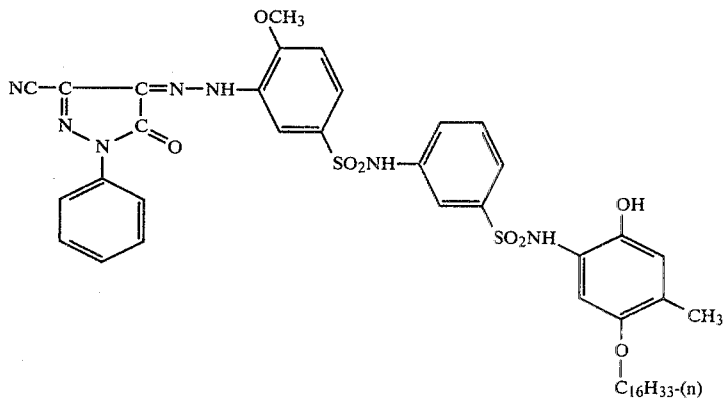

1.5 g/m² of N,N-diethyllaurylamide, 1.5 g/m² of gelatin and 0.01 g/m² of 2,5-di-tert-octylhydroquinone.

(11) A layer containing a blue-sensitive internal latent image type silver iodobromide emulsion (containing 2 mol% of silver iodide, 1.1 g/m² of gelatin and 1.4 g/m² of silver), 0.03 g/m² of 2,5-di-tert-octylhydroquinone and 0.017 g/m² of 2-methyl-3-(2-formylethyl)benzothiazolium bromide.

(12) A layer containing 0.6 g/m² of gelatin.

(13) A cover sheet produced by coating on a transparent polyethylene terephthalate film support the following layers in the order listed:

(i) A neutralizing layer composed of 10 g/m² of polyacrylic acid.

(ii) A timing layer composed of 10 g/m² of acetyl cellulose.

A sealed container retaining the processing solution having the composition described below:

| Composition of Viscous Processing Solution | | |
|---|---|---|
| Water | 820 | ml |
| Sulfuric Acid (1N aq. soln.) | 5 | ml |
| Hydroxyethyl Cellulose | 60 | g |
| 4-Hydroxymethyl-4-methyl-1-phenyl-3-pyrazolidone | 5 | g |
| 5-Methylbenzotriazole | 2 | g |
| tert-Butylhydroquinone | 0.4 | g |
| Sodium Sulfate | 2 | g |
| Carbon Black | 150 | g |
| Sodium Hydroxide | 30 | g | was assembled in the light-sensitive film unit. The container was so designed and disposed that a certain portion of the container was easily ruptured and the processing solution would be spread between the above-described layer (12) and the cover sheet (13) when the film unit was passed through a pair of juxtaposed pressure-applying rollers.

The above-described light-sensitive film unit was image-wise exposed in a camera and passed through a pair of rollers to spread the processing solution whereby transferred dye images were obtained. The cyan transferred image was particularly excellent of the transferred dye images from the standpoint of transferability and light fastness.

Similar preferred results were obtained when the Compounds (2), (3), (4) and (5) described above derived from the compounds of this invention as intermediates (cyan dye-releasing redox compounds) were respectively used in place of the above-described Compound (1).

REFERENCE EXAMPLE 2

The same procedures as described in Reference Example 1 were repeated except using the following known cyan dye-releasing redox compound:

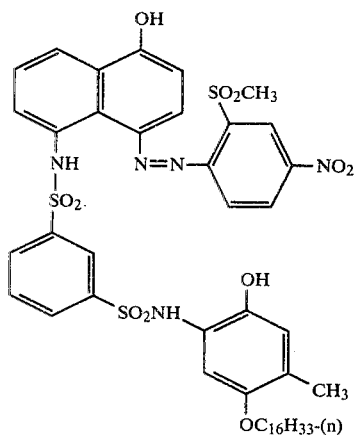

in place of Compound (1) and Compound (30) derived from the intermediate of this invention in place of the known magenta dye-releasing redox compound described above, respectively, whereby magenta transferred images having excellent transferability were obtained.

Similar advantageous results were obtained when Compounds (31), (32), (33) and (34) derived from the compounds of this invention as intermediates were respectively used in place of Compound (30).

REFERENCE EXAMPLE 3

The same procedures as described in Reference Example 1 were repeated except using Compound (37) derived from the intermediate of this invention in place of the known yellow dye-releasing redox compound described above and the known cyan dye-releasing redox compound used in Reference Example 2 in place of Compound (1), respectively, whereby yellow transferred images having excellent transferability were obtained.

Similar advantageous results were obtained when Compounds (38), (39), (40) and (41) derived from the compounds of this invention as intermediates were respectively used in place of Compound (37).

While the invention has been described in detail and with reference to specific embodiments thereof, it will be apparent to one skilled in the art that various changes and modifications can be made therein without departing from the spirit and scope thereof.

What is claimed is:

1. A compound suitable for use as an intermediate in the preparation of dye releasing redox compounds of improved transferability and light fastness for use in color diffusion transfer processes said compound being a 2-alkoxyalkoxy-5-nitrobenzenesulfonic acid or a salt thereof represented by the following general formula

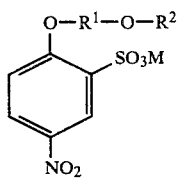

Wherein $R^1$ represents an alkylene group having 2 to 15 carbon atoms, with the proviso that when $R^1$ represents a branched chain alkylene group an acetal linkage is not formed; $R^2$ represents an alkyl group having up to 8 carbon atoms; and M represents a hydrogen atom or another cation capable of forming a salt with sulfonic acid.

2. The compound as claimed in claim 1, wherein $R^1$ is a group selected from the group consisting of a straight chain alkylene group of the formula $-(CH_2)_p-$ wherein p is an integer of 2 to 4, and a branched chain alkylene group having 3 to 4 carbon atoms.

3. The compound as claimed in claim 2, wherein $R^1$ is a $-CH_2CH_2-$ group.

4. The compound as claimed in claim 1, wherein $R^2$ is a group selected from the group consisting of straight chain or branched chain alkyl groups having 1 to 4 carbon atoms.

5. The compound as claimed in claim 1, wherein M is a hydrogen ion, an alkali metal ion or an alkaline earth metal ion.

6. The compound as claimed in claim 1, wherein M represents a pyridinium ion or a nucleus substituted derivative thereof or a quinolinium ion or a nucleus substituted derivative thereof.

7. The compound as claimed in claim 1, wherein $R^1$ is a $-CH_2CH_2-$ group; $R^2$ is selected from the group consisting of straight chain or branched chain alkyl groups having 1 to 4 carbon atoms, and M is an alkali metal ion.

8. The compound as claimed in claim 7, wherein $R^2$ is a straight chain alkyl group having 1 to 4 carbon atoms, and M is a sodium ion.

* * * * *